(12) United States Patent
Flynn et al.

(10) Patent No.: US 9,776,017 B2
(45) Date of Patent: Oct. 3, 2017

(54) METHOD AND SYSTEM FOR DYNAMICALLY-TRIMMED SPOT SCANNING FOR ION THERAPY

(71) Applicant: UNIVERSITY OF IOWA RESEARCH FOUNDATION, Iowa City, IA (US)

(72) Inventors: Ryan Flynn, Iowa City, IA (US); Daniel Hyer, Iowa City, IA (US); Dongxu Wang, Iowa City, IA (US); Patrick Hill, Iowa City, IA (US); Yves Claereboudt, Nil-St-Vincent (BE)

(73) Assignee: University of Iowa Research Foundation, Iowa City, IA (US)

(*) Notice: Subject to any disclaimer, the term of this patent is extended or adjusted under 35 U.S.C. 154(b) by 0 days.

(21) Appl. No.: 14/897,077

(22) PCT Filed: Jul. 3, 2014

(86) PCT No.: PCT/US2014/045363
§ 371 (c)(1),
(2) Date: Dec. 9, 2015

(87) PCT Pub. No.: WO2015/003111
PCT Pub. Date: Jan. 8, 2015

(65) Prior Publication Data
US 2016/0199667 A1 Jul. 14, 2016

Related U.S. Application Data

(60) Provisional application No. 61/843,092, filed on Jul. 5, 2013, provisional application No. 61/900,455, filed on Nov. 6, 2013, provisional application No. 61/946,074, filed on Feb. 28, 2014.

(51) Int. Cl.
*A61N 5/10* (2006.01)
*G21K 1/04* (2006.01)
*G21K 1/10* (2006.01)

(52) U.S. Cl.
CPC ........... *A61N 5/1043* (2013.01); *A61N 5/103* (2013.01); *G21K 1/04* (2013.01); *G21K 1/10* (2013.01); *A61N 2005/1076* (2013.01); *A61N 2005/1087* (2013.01); *A61N 2005/1095* (2013.01)

(58) Field of Classification Search
None
See application file for complete search history.

(56) References Cited

U.S. PATENT DOCUMENTS

| | | | |
|---|---|---|---|
| 5,668,371 A * | 9/1997 | Deasy | A61N 5/1042 250/505.1 |
| 6,891,177 B1 | 5/2005 | Kraft et al. | |
| 7,132,674 B2 * | 11/2006 | Pastyr | G21K 1/04 250/492.1 |
| 7,763,873 B2 * | 7/2010 | Flynn | A61N 5/10 250/396 R |
| 7,826,593 B2 | 11/2010 | Svensson et al. | |
| 8,232,536 B2 | 7/2012 | Harada | |

(Continued)

*Primary Examiner* — Jack Berman
(74) *Attorney, Agent, or Firm* — Smith, Gambrell & Russell

(57) ABSTRACT

A spot scanning (SS) ion therapy system configured for dynamic trimming of an ion particle pencil beam to reduce the amount of the radiation dosage outside of a target boundary.

33 Claims, 29 Drawing Sheets

(56) References Cited

U.S. PATENT DOCUMENTS

| | | | |
|---|---|---|---|
| 8,269,196 B2* | 9/2012 | Hill .................. | A61N 5/1042 250/492.3 |
| 8,565,378 B2* | 10/2013 | Echner ............... | A61N 5/1042 378/148 |
| 2013/0056646 A1 | 3/2013 | Iwata | |
| 2015/0174429 A1* | 6/2015 | Zwart ................. | A61N 5/1043 250/396 R |

* cited by examiner

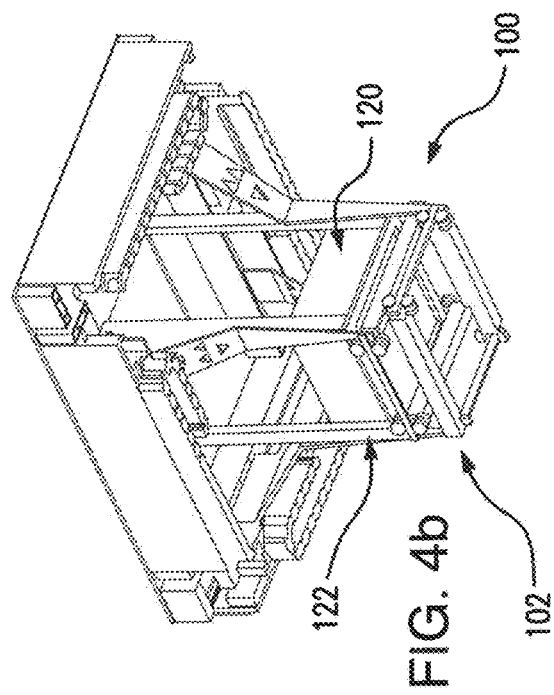
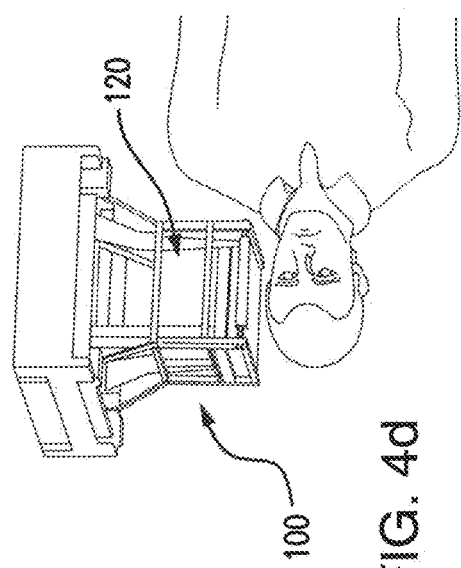
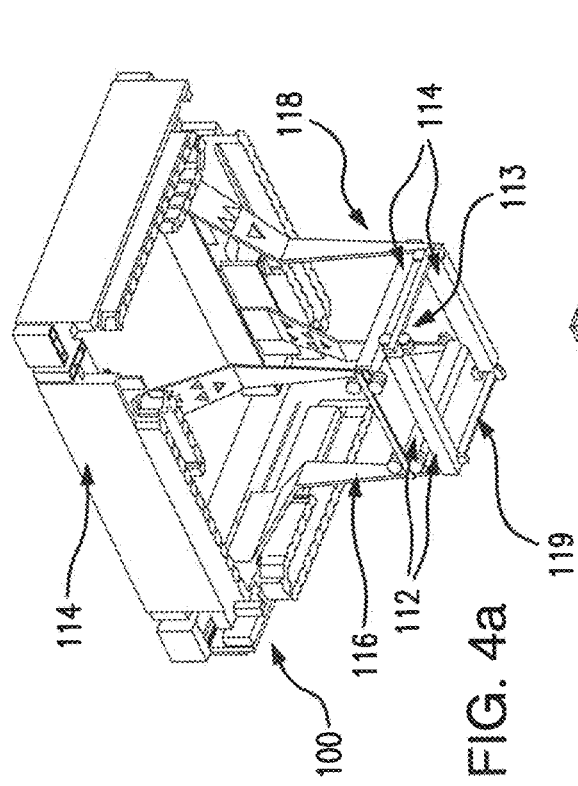
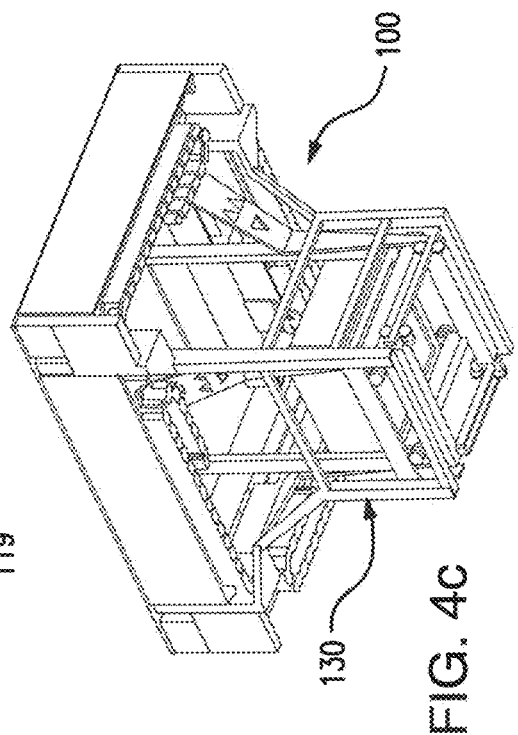

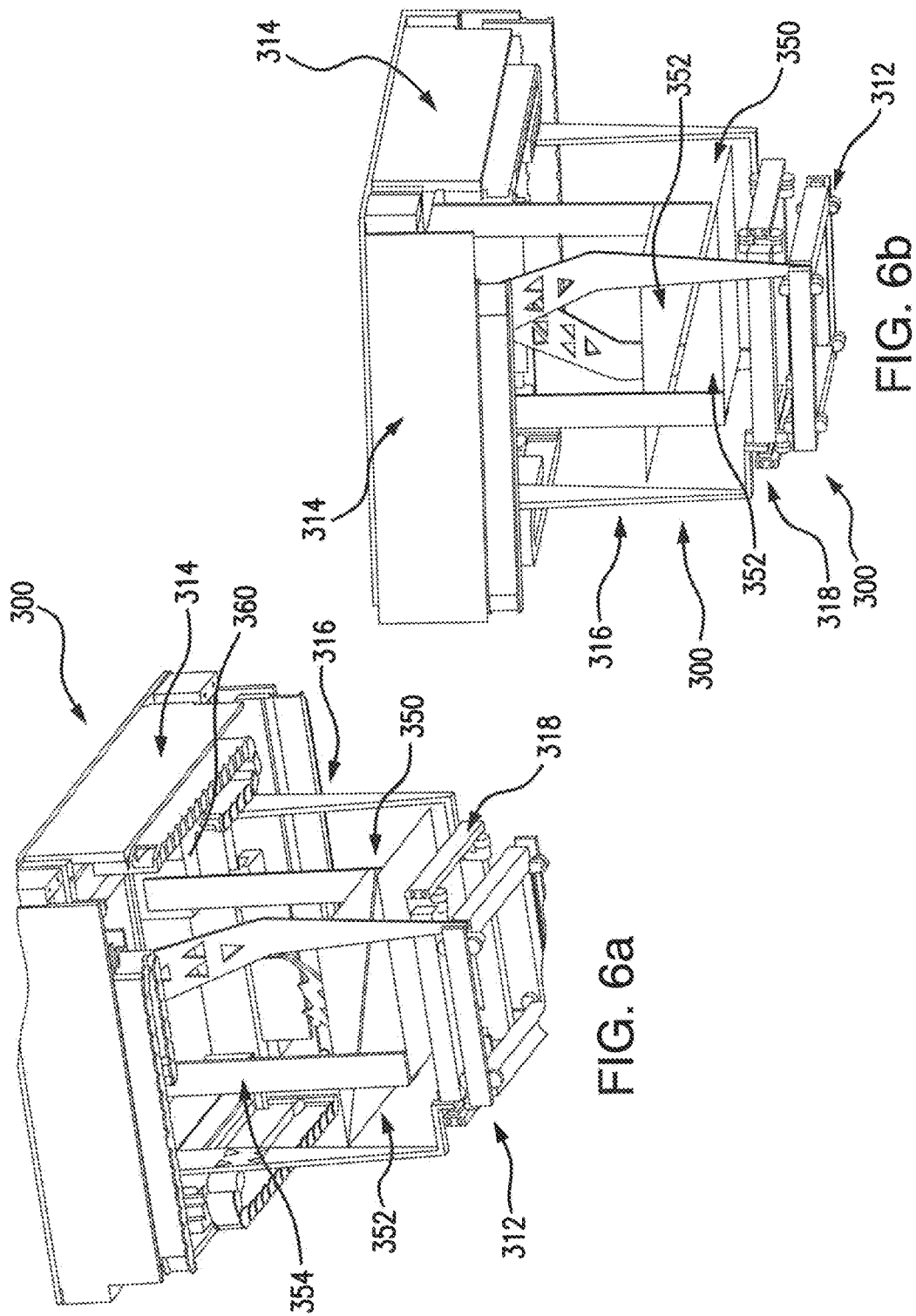

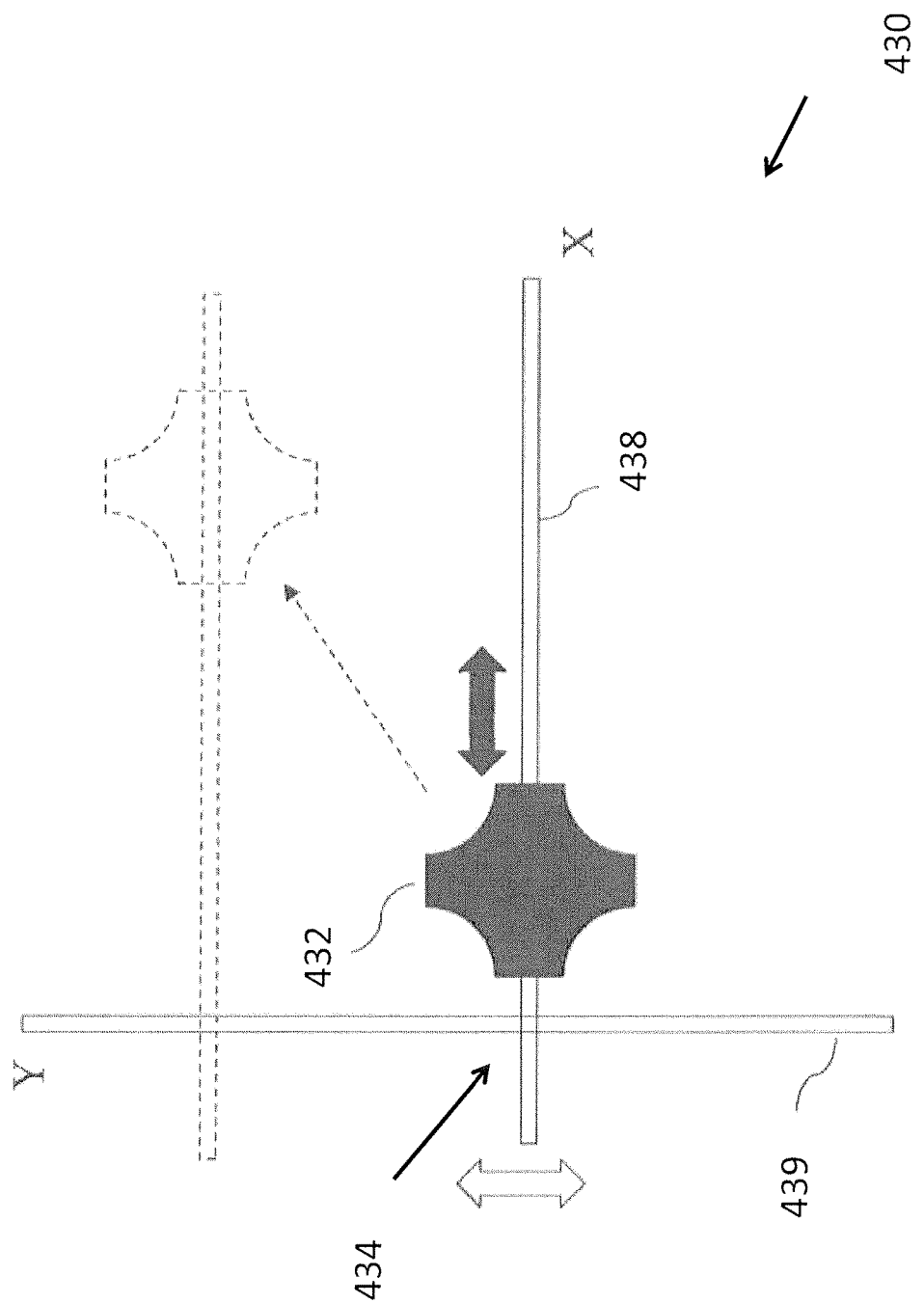

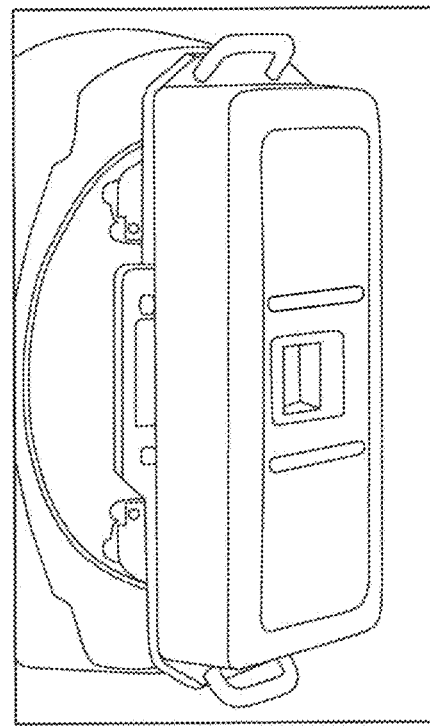
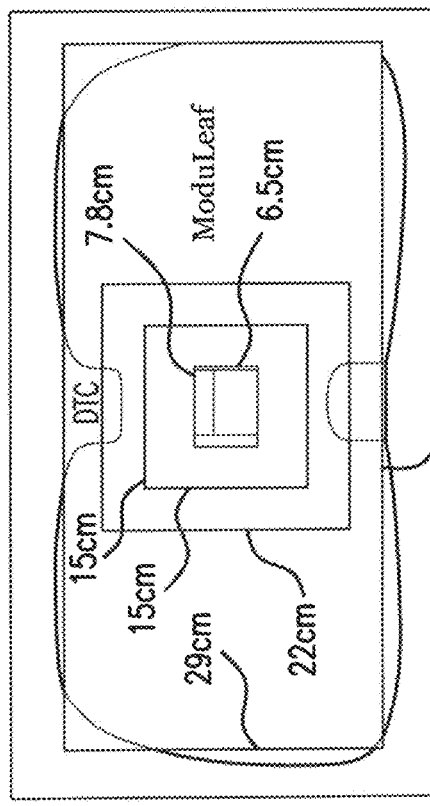
FIG. 19a
FIG. 19b

METHOD AND SYSTEM FOR DYNAMICALLY-TRIMMED SPOT SCANNING FOR ION THERAPY

CLAIM OF PRIORITY

This application claims priority from U.S. Provisional Patent Application No. 61/843,092 filed on Jul. 5, 2013, U.S. Provisional Patent Application No. 61/900,455, filed on Nov. 6, 2013, and U.S. Provisional Application No. 61/946,074 filed on Feb. 28, 2014, all of which are relied upon and incorporated herein in their entirety by reference.

BACKGROUND OF THE INVENTION

Technical Field

The invention relates to the field of charged particle radiation therapy. More specifically, the invention relates to the field of spot scanned ion therapy. More specifically, the invention relates to a charged particle system for the irradiation of a target of tissues that may be cancerous. The invention also relates to a method for irradiation of a target with a particle pencil beam.

Related Art

In charged particle radiation therapy, a number of irradiation techniques are known today. The most common form of radiation therapy currently is photon therapy. However, photon therapy comes with several complications. For one, when using photon therapy, the applied photon beam passes through a targeted tumor and exits the patient through healthy tissue distal to the tumor. The exiting of the photon beam or dose through the healthy tissue increases the difficulty in preventing radiation damage to the healthy tissue. The radiation damage caused by the exiting dose through healthy tissue also is a limiting factor when designing an effective tumor treatment plan.

Ion therapy, which includes proton therapy and argon, carbon, helium and iron ion therapy, amongst others, provides some advantages over photon therapy. For one, ion therapy can result in a lower total radiation energy, termed integral dose, being deposited in a patient for a given tumor dose in relation to photon therapy. The integral dose reduction is significant because it reduces the probability of stochastic effects, i.e., patients developing secondary malignant neoplasms following irradiation of non-tumor tissue. Young patients with high probabilities of long term survival have a higher probability of developing secondary malignant neoplasms than older patients since the probability of development is related to the time elapsed post-therapy. Thus, the reduction of radiotherapy doses to non-tumor tissues in children is a particularly important advantage of ion therapy. The integral dose reduction for proton therapy relative to photon therapy has been quantified for parameningeal paraorbital rhabdomyosarcoma and spinal neuraxis in children with medulloblastoma, resulting in a reduction in the probability of radiation-induced secondary malignancies by factors of ≥2 and 8-15, respectively. Proton therapy is expected to reduce the probability of occurrence of secondary malignant neoplasms in adults as well. For example, the probability of a secondary malignant neoplasm is decreased by 26% to 39% for prostate patients receiving proton therapy versus intensity modulated photon therapy.

The second clinical advantage of ion therapy over photon therapy is that radiation dose to healthy tissues is reduced sufficiently such that deterministic effects (i.e., complications whose magnitude is related to the radiation dose delivered) may be reduced relative to photon therapy. Examples of deterministic effects are skin erythema and xerostomia. The reduction in deterministic effects has been demonstrated in multiple studies in which tumor dose conformity has been shown to be comparable to that of photon therapy, but healthy tissue sparing for proton therapy is superior. Healthy tissues associated with multiple tumor sites have been shown to be spared of more dose by proton than photon therapy, including paraspinal sarcomas, head-and-neck malignancies, meningioma, cervix, medulloblastoma, paranasal sinus, and prostate.

Spot scanning (SS), an advanced form of ion therapy delivery, has some advantages over traditional ion therapy. Conventional proton therapy beams for treating patients are typically generated using either passive scattering or uniform dynamic scanning. With passive scattering, one or more range compensators and a range modulator are used to spread a proton pencil beam into a beam that produces a spatially uniform dose distribution laterally and in depth. The range modulator may be a spinning propeller, wedge, or ridge filter, and produces a spread out Bragg peak (SOBP). The field is shaped laterally to the central beam axis with a custom-designed aperture, block, or multi-leaf collimator (MLC), and is shaped in depth to match the distal edge of the treatment volume using a patient-specific compensator. Single and double scattering systems exist, the latter typically providing larger regions of uniform dose than the former. Uniform dynamic scanning uses a magnetically scanned pencil beam and dynamic energy modulation to generate proton fields which, when averaged over time, have a uniform intensity in space. Field shapes are defined by apertures or blocks in a similar manner as with passive scattering.

In SS ion therapy, the treatments are delivered with pencil beams, usually produced by a beam generator (e.g., a cyclotron), that are magnetically scanned to deliver dose in the target. The size of the pencil beam in SS is generally much smaller than uniform dynamic scanning. The use of pencil beams allows the beam shape to be defined using the scanning magnets rather than an aperture. This pencil beam spot scanning technique represents an advance over the single or double scattering technique, wherein a scattered broad beam is shaped by a patient specific collimator or aperture, so that it corresponds to the shape of the target to be treated. As a result, the lateral falloff of dose distributions delivered with spot scanning without an aperture is dependent on the size of the incoming pencil beam and interactions of the beam in the patient.

Additionally, in SS, the beam intensity, when averaged over time, is not required to be uniform. This allows intensity modulated proton therapy (IMPT) to be delivered. With IMPT, several fields can be optimized simultaneously such that the sum of all fields will yield a uniform dose to the target while minimizing the dose to surrounding normal structures.

However, proton SS systems have low-energy (≤160 MeV) lateral beam intensity profiles that are less sharp than those of photon therapy systems, thus more of the radiation dose is typically deposited lateral to the tumor for low-energy treatments (i.e., the lateral penumbra of a pencil beam is larger than the penumbra of a collimated broad beam). As a result, proton SS is superior to photon therapy in integral dose delivered and inferior to conventional proton therapy in dose delivered lateral to the tumor for low-energy treatments. The degree of inferiority imposed by the latter property is dependent upon the energy of the ion beam, as low energy beams tend to be broader than higher energy beams due to the physical properties of the system used to transport the ion beam from the accelerator to the patient.

Therefore, attempts have been made to reduce the size of the penumbra. For example, a device to reduce the penumbra of a pencil beam spot scanning is disclosed in U.S. Patent Application Publication No. US 2013/0043408. However, the device consists of a patient specific collimator or aperture to be inserted in the beam line. A patient specific collimator means an individual collimator for each patient has to be constructed, adding to the overall cost of treatment. MLCs have been used with pencil beam spot scanning, but MLCs are complex to develop and require a lot of space such that MLCs are prevented from being positioned in a very close proximity to the patient. In addition, the weight of such an MLC requires a strong mechanical structure to support it.

Therefore, there is a need for a system and method for the application of SS ion therapy that reduces the radiation dose delivered to healthy tissues outside the target boundary. In addition, there is a need for a system that allows the application of SS ion therapy at areas of a patient in which access is difficult (e.g., areas around the neck and head due to the location of the patient's shoulders). There is also a need for a simplified and cost effective device for reducing the lateral penumbra of a beam from a SS system.

SUMMARY OF THE INVENTION

It is an object of the invention to provide a particle radiation therapy system for irradiation of a target through spot scanning that reduces the delivery of dose outside the target boundary. A further objective is to provide a compact system for delivery of spot scanning (SS) therapy to difficult areas of a patient.

The invention is a system and process for improving SS ion therapy by reducing the delivery of the SS ion therapy dose outside of the target boundary. In an exemplary aspect, the invention improves SS ion therapy of cancerous tumors by reducing the radiation dose delivered to healthy tissues lateral to the target.

In an aspect, the SS ion therapy is delivered by an ion therapy source. In an exemplary aspect, the ion therapy source produces a particle pencil beam. In an aspect, the particle pencil beam can be characterized by a phase space. In an aspect, the ion therapy source of the system comprises a beam generator for generating the pencil beam. In an aspect, the ion therapy source of the system further comprises a spot scanning system configured for performing a number of spot irradiations by sequentially directing and delivering said pencil beam to a number of spot locations in said target. In such aspects, the spot scanning system can comprise one or more scanning magnets.

In an aspect, the system delivers Dynamically-Trimmed Spot Scanning (DTSS). In such aspects, the system includes an irradiation controller for controlling the delivery of a dose during said spot irradiations and a beam intercepting system for intercepting a portion of the pencil beam during one or more of the number of spot irradiations so as to modify the phase space of the pencil beam. The beam intercepting system of DTSS system can include a dynamic trimming collimator (DTC) that is configured to intercept a portion of the pencil beam that shapes the particle pencil beam. In such aspects, the DTC is located downstream of the one or more scanning magnets of the spot scanning system.

In an aspect, the DTC can comprise at least one trimmer configured to intercept the beam. In an aspect, the beam intercepting element can comprise a thickness and shape adapted for changing the phase space of the pencil beam. Depending on the thickness and shape of the at least one trimmer, the transverse beam phase shape and/or longitudinal beam shape can be changed. In an aspect, the thickness and the shape of the at least one trimmer is configured to block a portion of the pencil beam so as to change the transverse beam size of the pencil beam. In another aspect, the thickness and shape of the at least one trimmer can be configured to modify the energy and/or energy spread of the pencil beam. In another aspect, the thickness and the shape of the at least one trimmer is configured to modify the energy and/or energy spread of the pencil beam. In an exemplary aspect, the thickness and shape of the at least one trimmer is configured to both changes the transverse beam size and the energy and/or energy spread of the pencil beam.

In an aspect, the at least one trimmer can be configured to move along a first axis of motion and a second axis of motion to intercept a portion of the pencil beam. In an aspect, the trimmer can be configured to move across axes that are perpendicular to the central axis of the pencil beam. In an aspect, the trimmer can be configured to move along an axis that is parallel to the central axis of the pencil beam. In an aspect, the movement of the trimmer can be done through a driving mechanism configured to support the at least one trimmer.

In an aspect, the at least one trimmer can comprise a plurality of trimmers. In an aspect, each of the trimmers is mounted to a driving mechanism. During the ion therapy, the trimmers can move in synchrony with the scanned ion beam. In an aspect, the DTC can utilize a plurality of trimmers that are configured to rapidly move along a path perpendicular to the axis of a pencil beam. In an aspect, the DTC can include a driving controller for controlling the driving mechanism of each trimmer to place the trimmer at a pre-defined position for the interception of the pencil beam. The pre-defined positions can correspond to positions for intercepting the beam while performing a spot irradiation. In an aspect, the driving controller can include a control interface for receiving parameters for the positioning of the trimmer along the first axis and second axis of motion. In an exemplary aspect, the parameters can include at least first and second parameters for the first and second axes. In an aspect, the DTSS can include a position planning controller configured for defining, for one or more of the spot irradiations, corresponding pre-defined positions for positioning the at least one trimmer.

In an aspect, the first axis and the second axis may correspond to two non-parallel translation axes. In such aspects, the first parameter and the second parameter may correspond to coordinate positions along the translation axes. In another aspect, the first axis and the second axis may correspond to a translation axis and a rotation axis. In such an aspect, the rotation axis is preferably essentially perpendicular to the translation axis. Further, in such an aspect, the first parameter corresponds to a coordinate position along the translation axis and the second parameter corresponds to a rotation angle with respect to the rotation axis.

It is an advantage of embodiments of the present invention that by using a first and second axes of motion allows for the same at least one trimmer to be moved to various pre-defined positions for intercepting the pencil beam. The interception of the pencil beam can be defined by defining the exact position of the trimmer within pencil beam.

In an aspect, the DTC can be configured to be small enough to position the trimmers within several centimeters of the patient's skin, even when treating sites such as the head and neck. In an aspect, the ability to be able to position the trimmers in various positions multiple times allows for a minimal number of trimmers to be used, reducing the overall size of the DTC.

In another aspect, the trimmer rods can be configured to partially block the ion beam, which can increase the sharpness of the beam. The increase in beam sharpness results in a concurrent decrease in the radiation dose that spills laterally out of the target tissue and into adjacent normal tissue. Such an improvement is useful in the field of radiation oncology, as DTSS is a solution to the well-known problem that shallowly-penetrating ion beams, especially proton beams, deliver lateral radiation doses that are inferior to those of photon therapy.

In an aspect, the driving controller can be configured to interface with an irradiation controller for receiving a signal indicating a beam on/beam off status information and whereby the driving controller is configured to allow motion of the trimmer only when the beam is in an off status. In other words, the trimmer is only moved in between spot irradiations and not during spot irradiations. In such aspects, a simplified irradiation control system can be utilized.

These and other objects and advantages of the invention will become apparent from the following detailed description of the preferred embodiment of the invention. Both the foregoing general description and the following detailed description are exemplary and explanatory only and are intended to provide further explanation of the invention as claimed.

The accompanying drawings are included to provide a further understanding of the invention and are incorporated in and constitute part of this specification, illustrate several embodiments of the invention, and together with the description serve to explain the principles of the invention.

BRIEF DESCRIPTION OF THE FIGURES

FIGS. 4a-d are perspective views of components of a dynamic trimming collimator according to an aspect of the present invention.

FIGS. 6a-b are perspective views of a dynamic trimming collimator according to an aspect.

FIG. 7 is a schematic representation of a dynamic trimming collimator according to an aspect.

FIGS. 19a&b are images of a Siemens ModuLeaf system and Radionics MMLC.

DETAILED DESCRIPTION OF THE INVENTION

Figure 1:
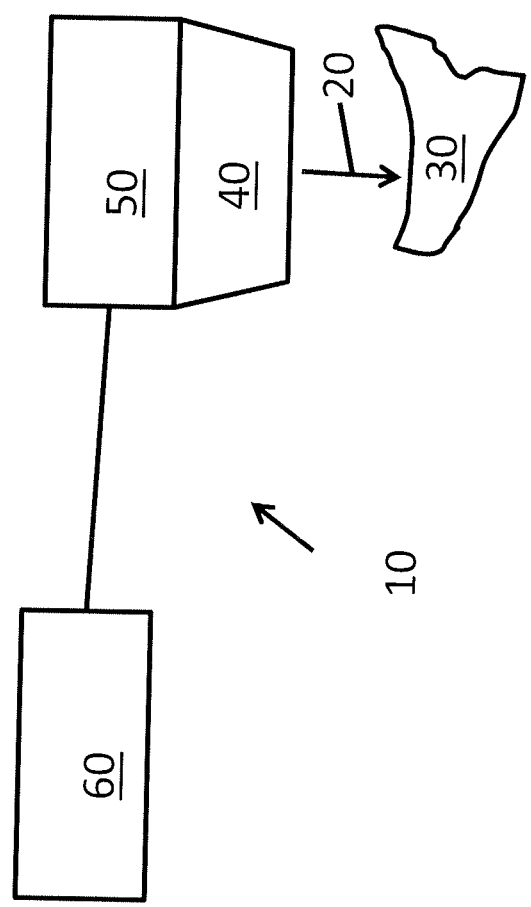
FIG. 1 is a schematic diagram of a spot scanning (SS) ion therapy system according to an aspect of the present invention.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

As will be appreciated by one skilled in the art, aspects of the current invention may take the form of an entirely hardware embodiment, an entirely software embodiment, or an embodiment combining software and hardware aspects. In an aspect, the current invention can include a combination of physical components configured to perform certain steps and functions (e.g., generating ion beams, moving trimmers configured to shape ion beams, etc.) that are controlled by a combination of hardware and software components. Furthermore, components of the methods and systems may take the form of a computer program product on a computer-readable storage medium having computer-readable program instructions (e.g., computer software) embodied in the storage medium. Any suitable computer-readable storage medium may be utilized including hard disks, CD-ROMs, optical storage devices, or magnetic storage devices.

Further, components and methods utilized by the present invention as described below can be performed in a program environment, which may incorporate a general-purpose computer or a special purpose device, such as a hardware appliance, controller, or hand-held computer. In addition, the techniques of the components described herein can be implemented using a variety of technologies known in the art. For example, the methods may be implemented in software executing on a computer system, or implemented in hardware utilizing either a combination of microprocessors or other specially designed application specific integrated circuits, programmable logic devices, or various combinations thereof.

Some aspects of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer readable memory that can direct a computer or other programmable data processing apparatus to function in a particular manner, such that the instructions stored in the computer-readable memory produce an article of manufacture including computer readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions, and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

As illustrated in FIGS. 1-27, aspects of the present invention are directed at a charged particle radiation system 10. In an exemplary aspect, the charged particle radiation system 10 comprises a spot scanning (SS) ion therapy system 10 configured to apply ion therapy 20 on at least one target 30 with a reduction of the radiation outside of the target zone. In an exemplary aspect, the SS ion therapy system 10 is configured to apply the ion therapy 20 on cancerous targets 30 while reducing the dose delivered to healthy tissues lateral to the target. In an aspect, the SS ion therapy system 10 is configured to deliver Dynamically-Trimmed Spot Scanning (DTSS). The SS ion therapy system 10 utilizes a dynamic trimming collimator (DTC) 40 to apply the ion beam 20 from an ion therapy source 50 in a narrowly focused manner. During DTSS delivery, a narrow ion beam 20 with a given energy, which determines the penetration depth, is magnetically scanned by components of the ion therapy source 50 across a patient's target volume. The scanning pattern is often in a line-by-line raster pattern, but can be arbitrarily defined to deviate from a raster pattern. However, since the ion therapy source 50 cannot perfectly focus the beam 20 on a target 30, when the beam 20 is placed near the edge of the target, some radiation dose spills outside of the target and into normal tissue. The DTC 40 assists the ion therapy source 20 by limiting such spillage of radiation. In other words, the DTC 40 enables the delivery of DTSS radiation dose distributions that spare normal tissue adjacent to tumors/targets 30 more effectively than the dose distributions generated by conventional SS. A system controller 60 can control the operation of the DTC 40 and the ion therapy source 50, as shown in FIGS. 1 and 2, discussed in more detail below.

Figure 2:
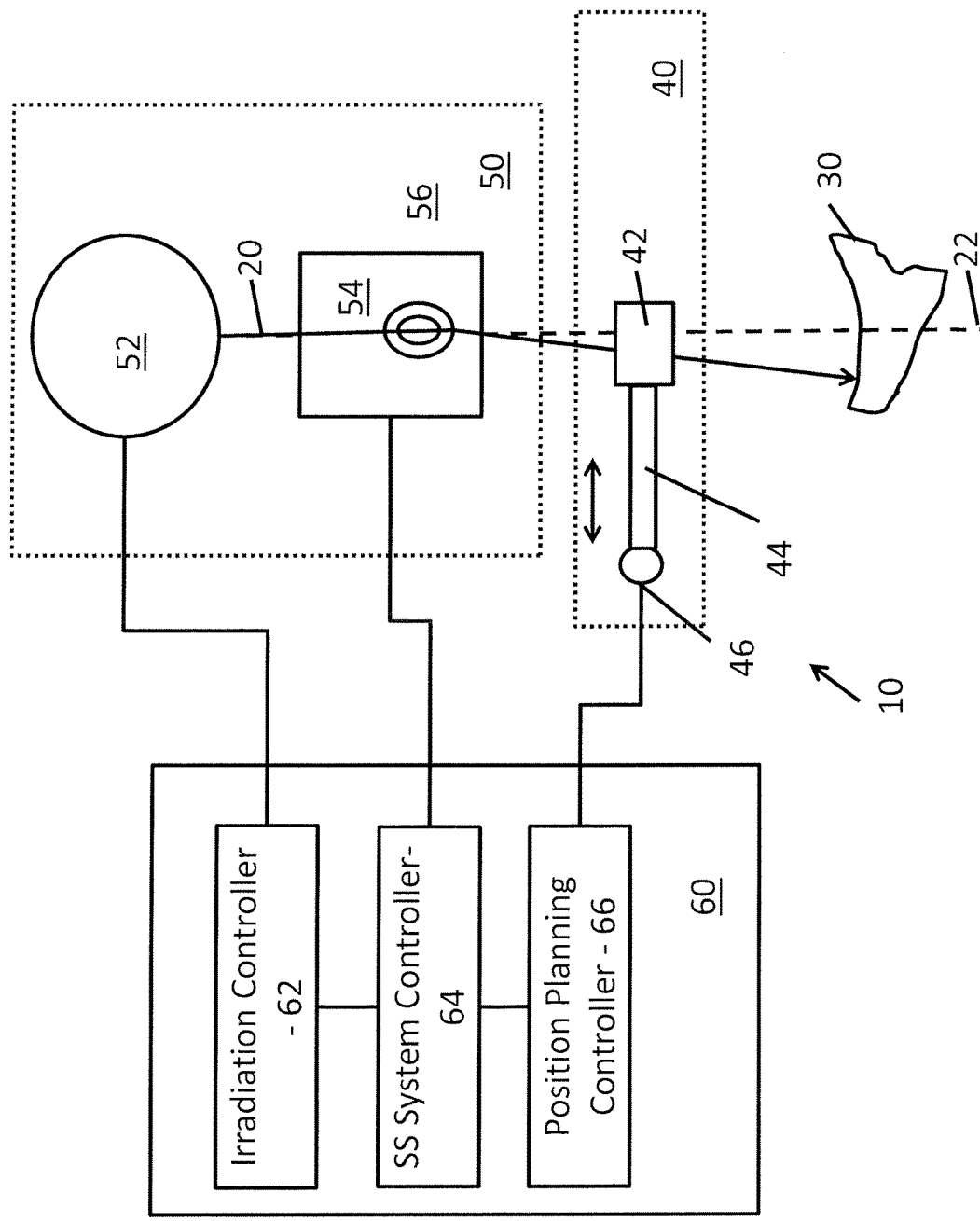
FIG. 2 is a schematic diagram of the SS ion therapy system of FIG. 1.

As shown in FIG. 2, the ion therapy source 50 of the SS ion therapy system 10 comprises a beam generator 52 for generating the ion beam 20 for use with spot scanning. In an aspect, the beam generator 52 is configured to generate a proton particle pencil beam 20. The ion particle pencil beam 20 can have a wide range of energy. As known, the energy of the particle pencil beam 20 can determine the penetration depth of the beam 20 within the target 30, discussed in detail below. In an aspect, an irradiation controller 62 can be configured to control the delivery of a radiation dose to the various spot locations of the target 30. In an aspect, the irradiation controller 62 can take the form of a module 62 within the system controller 60 of the SS ion therapy system 10.

In an aspect, the particle pencil beam 20 is characterized by a beam phase space. The beam phase space can be defined at given positions along a traveling path of the beam. As well known in particle beam optics, the beam phase space of an energetic particle beam is defined through the position distribution and momentum distribution of the particles within the beam. In general, the phase space can be divided in a transverse beam phase space and a longitudinal beam phase space. The transverse phase space defines the transverse extension of the beam 20 with respect to a central travelling direction, or central axis 22, of the beam. A physical quantity that can for example be measured is the transverse beam size. In the longitudinal direction, perpendicular to the transverse direction, the longitudinal phase space can be defined by the averaged particle energy or averaged momentum in the beam travelling direction and by the associated energy spread or momentum spread.

In an aspect, the ion therapy source 50 further includes a spot scanning system 54 configured for performing a number of spot irradiations by sequentially directing and delivering the ion beam 20 to a number of spot locations in the target 30. In an aspect, the spot scanning system 54 includes means for scanning the pencil beam 20 over the target 30. In an aspect, the spot scanning system 54 includes one or more electromagnets 56 designed for scanning the particle beam 20 over the target 30. In an aspect, the at least one electromagnet 56 comprises two electromagnets 56 for scanning in an X and Y directions, respectively. In another aspect, a single scanning magnet 56 configured to scan in the X and Y directions can be used. In an additional aspect, the scanning magnets can be superconducting. A spot scanning (SS) system controller 64 can be utilized to control the spot scanning system 54, including the positioning of the scanning magnets. In an aspect, the SS system controller 64 can take the form of a module within the system controller 60. In another aspect, the irradiation controller 62 can be configured to control the operations of the spot scanning system 54 and the SS system controller 64.

As illustrated in FIGS. 1-2, the SS ion therapy system 10 of the present invention includes a dynamic trimmer collimator (DTC) 40. The DTC 40 is configured to intercept a portion of the pencil beam 20 during a spot irradiation so as to modify the phase space of the pencil beam 20. In an aspect, the DTC 40 is located downstream of the spot scanning system 54. In an exemplary aspect, the DTC 40 is located downstream of the scanning magnets 56 of the spot scanning system 54.

In an aspect, the DTC 40 includes at least one trimmer 42 that is located downstream of the magnet(s) 56 of the spot scanning system 54. In an aspect, the at least one trimmer 42 is configured to intercept a portion of the pencil beam 20. In an aspect, the trimmer 42 has a thickness and shape for changing the phase space of the pencil beam 20. In an aspect, the thickness of the trimmer 42 will depend on the energy of the pencil beam 20 that is utilized by the system 10. In an aspect, the proton energies for use in proton therapy can vary between 70 MeV and 250 MeV. The thickness of the trimmer 42 can be selected to, for example, block particles having an energy lower than 160 MeV.

In an aspect, the trimmer 42 can be supported by a driving mechanism 44. In an aspect, the driving mechanism is configured to move the trimmer 42. In an aspect, the driving mechanism 44 is configured to have at least two degrees of freedom for moving the trimmer 42 to a pre-defined position for intercepting a portion of the pencil beam 20 during a spot irradiation. In such aspects, the driving mechanism comprises a first axis of motion and a second axis of motion configured for moving the trimmer 42 to a pre-defined position for intercepting a portion of the pencil beam 20 during the spot irradiation.

In an aspect, the trimmer 42 can either change the transverse beam phase space or the trimmer 42 can change the longitudinal beam phase space, depending on the geometry of the trimmer 42. For example, if a trimmer 42 has a water equivalent thickness that is larger than the water equivalent range of the pencil beam 20, then, by partially inserting the trimmer 42 into the pencil beam 20, part of the pencil beam 20 will be stopped in the trimmer 42 so that the remaining portion of the beam 20 has a modified transverse phase space. For example, by cutting part of the beam 20 laterally, the lateral beam shape of the pencil beam 20 can be modified. In this way, the lateral penumbra can be improved.

Alternatively, in another aspect, by using a trimmer 42 that includes portions having a water equivalent thickness that is smaller than the water equivalent range of the pencil beam 20, the pencil beam 20 will not be stopped in such portions of the trimmer 42, but the remaining pencil beam 20 will have a modified longitudinal phase space. For example, the energy of the remaining beam can be shifted by a given amount or the energy distribution of the remaining beam can be modified. For modifying the longitudinal phase space, the trimmer 42 can have either a fixed constant thickness (e.g., a trimmer 42 with a rectangular shape) or it can have a variable thickness. For example, a trimmer 42 having a variable thickness (e.g., a trimmer 42 having a triangular shape) can be used to allow varying the longitudinal phase space relative to the position of the pencil beam 20 and the trimmer 42. In an aspect, the trimmer 42 can be configured to intercept only a portion of the pencil beam 20. In another aspect, the trimmer 42 can be configured to intercept the entire pencil beam 20.

In an aspect, the axis of motion of the driving mechanism 44 can be a translation axis. In another aspect, the axis of motion can be a rotation axis. Detailed embodiments using either multiple translation axes or using a combination of translation axes, rotation axes, or others, will be described below. The driving mechanism 44 can include, but is not limited to, electrical motors, hydraulic motors, and the like. In an exemplary aspect, the driving mechanism 44 is configured to move in at least two axes of motion such as to move the trimmer 42 within a plane that is essentially perpendicular to the central beam axis 22 of the pencil beam 20. In another aspect, the driving mechanism 44 can be configured to move the trimmer 42 on curved surface intersecting the central beam axis 22 of the pencil beam 20.

In an aspect, the DTC 40 can include a driving controller 46 that is configured to control the driving mechanism 44. In an exemplary aspect, the driving controller 46 can comprise a control interface (not shown) configured to receive a first parameter for the first axis of motion and a second parameter for the second axis of motion that defines the position of the trimmer 42. The system 10 can have a driving controller 46 for each of the driving mechanisms 44 employed, or there can be one driving controller 46 to control all of the driving mechanisms 44.

In an aspect, the SS ion therapy system 10 includes a position planning controller 66 configured for defining, for one or more of the spot irradiations, corresponding predefined positions for positioning the trimmer 42 during a spot irradiation so as to intercept the pencil beam 20. In an aspect, the position planning controller 66 can be configured to interact with the interface of the driving controller 46. In an aspect, the position planning controller 66 can be a module within the system controller 60. In other aspects, the position planning controller 66 can be a stand-alone controller/computer. In other aspects, the position planning controller 66 can be a controller can be a part of a treatment planning system. In an aspect, the driving controller 46 can be configured to interface with the irradiation controller 62 for receiving a signal indicating a beam on/beam off status. In such an aspect, the driving controller 46 can be configured to allow the motion of the trimmer 42 only when the beam 20 is in an off status, as indicated by the irradiation controller 62.

Figure 3:
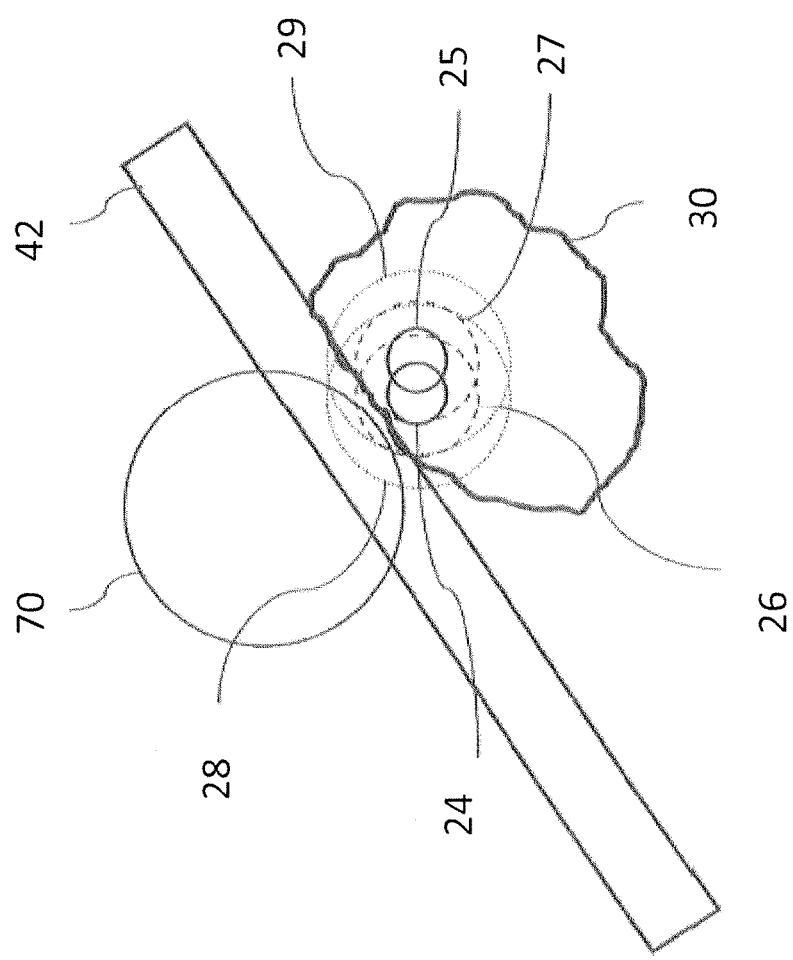
FIG. 3 is a schematic representation of the principle of using a trimmer to intercept a pencil beam according to an aspect of the present invention.

The use of a trimmer 42 according to the invention is illustrated in FIG. 3, showing two spot irradiations of a target 30. As illustrated, a rectangular shaped trimmer 42 is positioned in a pre-defined position to avoid the beam 20 hitting an at-risk organ 70 positioned near the target 30. In an aspect when the particle pencil beam 20 has a Gaussian lateral shape, the beam spot locations on the target 30 are visualized by showing the one sigma beam radius 24, 25 of the two adjacent beam spots. In addition, the two sigma radius 26, 27 and the three sigma radius 28, 29 of the two beams are shown. When the two exemplary spot locations are irradiated, the trimmer 42 will block part of the two sigma 26, 27 and three sigma 28, 29 lateral beam extensions and as a result prohibit the irradiation of the organ at risk 70. In this example, the pre-defined positions of the trimmer 42 for the two beam spot locations are the same. In other words, in this example, the trimmer 42 is maintained in the same position when irradiating the two beam spot locations. In another aspect, the trimmer 42 can be moved in between two spot locations to a different pre-defined location in order to optimize the intercepting effect and spare healthy tissue outside the target boundaries, discussed in more detail below.

According to an aspect, as illustrated in FIGS. 4a-d, the SS ion therapy system utilizes a DTC 100 to sharpen the ion beam (not shown). According to an aspect, the DTC 100 is configured to assist the ion therapy source (i.e., an ion source; not shown) to deliver a focused narrow ion beam. In an aspect, the ion therapy source can be selected based upon the ability to produce relatively low-energy ion beams. In an exemplary aspect, the ion therapy source is capable of producing energies ≤160 MeV at the patient surface for proton beams. Such energy levels are required for treating superficial targets but result in increased beam sizes due to the ion beam delivery technology. While a proton therapy source capable of producing energies greater than 160 MeV can be used with the DTC 100, at higher energies, the lateral spread of the proton beam is largely dependent on scattering in the patient and not on the ion beam delivery technology. Therefore, the DTC 100 can be most useful for proton energies <160 MeV where reduction in the lateral spread of the incoming beam will have an impact on the dose distribution in the patient.

By operating at these energy levels, the radiological thickness of trimmers 112 (discussed below) can be slightly greater than that of the range of a low energy proton beam, allowing the trimmers 112 to be lightweight compared to traditional collimators, such as the multi-leaf collimators (MLCs) used in photon and ion therapy. However, in other embodiments, other ranges of energy production can be used, which can require trimmers 112 of a greater thickness to be used, requiring more powerful driving mechanisms, discussed in more detail below.

In an aspect, the DTC 100 comprises a plurality of trimmers 112. The trimmers 112 can described as rod-like devices that are utilized by the DTC 100 to shape the ion beam employed by the ion therapy source. In an exemplary aspect, the DTC 100 includes four trimmers 112. In the exemplary aspect, the four trimmers 112 comprise a rectangular shape. In other embodiments, the shape of the trimmers 112 can include, but are not limited to, cylindrical, triangular, hexagonal, and the like. However, it is desired that the trimmer 112 have a length that is much greater than the width or height. A longer length is desired so that a trimmer 112 does not need to move along the direction of the length, but only needs to move in one direction. A rectangular shape is desired because it is easy to precisely control a rectangular trimmer 112 to trim an ion spot at a desired location. The height of the trimmer 112 can be dictated by the energy of the ion beam (the trimmer 112 should be of sufficient thickness to completely block the ion beam and stop unwanted ions from reaching the patient). The width of the trimmer 112 can be dictated by the lateral size of the ion beam (the width should be sufficient to completely block the unwanted portion of the ion beam). The length of the trimmer 112 is used to define the useable field size, with the length being much longer such that usable field sizes can be defined to treat large targets. In an exemplary aspect, the cross section of each trimmer 112 can be 2 cm×2 cm. With the mass of each trimmer 112 being highly dependent on the cross section, and the ability to drive the trimmers quickly enough to deliver the DTSS, it is desirable to have a smaller cross sections.

In addition, in other embodiments of the present invention, the number of trimmers 112 employed by the DTC 100 can vary as well. However, the number of trimmers 112 should enable the DTC 100 to assist in the shaping the beam of the ion therapy source effectively while keeping the weight of the DTC 100 low enough to enable the DTC 100 to be mounted to the ion therapy source. As in the exemplary aspect illustrated in FIGS. 4a-4d, four trimmers 112 is a logical number because the beam is scanned in a raster pattern and can be intercepted by the trimmers 112 as it arrives at each side of the target. More trimmers 112 could make the DTC 100 more bulky and without improving the dose distribution.

Referring back to FIGS. 4a-d, the trimmers 112 are associated with driving mechanisms 114. In an aspect, the driving mechanisms 114 can include linear motors 114. The trimmers 112 can be coupled to the driving mechanisms 114 through connecting rods 116. The DTC 100 can consist of four metal trimmers 112 with rectangular cross-sections, each of which can rapidly move along a path perpendicular to the axis of a narrow, scanned, ion beam. In an aspect, the DTC 100 can have a protruding nose 102 that is small enough to position the trimmers 112 within several centimeters of the patient's skin (see FIG. 4d), even when treating sites such as the head and neck. Such sites can be difficult to access due to the presence of the patient's shoulders. Each trimmer 112 is mounted to a driving mechanism 114, and during the ion therapy delivery process, the trimmers 112 move in synchrony with the scanned ion beam. The trimmers 112 partially block the ion beam at spatial locations where the patient would benefit from beam sharpening, such as at the tumor edges. This increase in beam sharpness results in a concurrent decrease in the radiation dose that spills laterally out of the target tissue and into adjacent normal tissue.

In an aspect, the trimmers 112 are comprised of metallic trimmers 112. The trimmers 112 can be comprised of a variety of metals. In an aspect, the trimmers 112 can include brass and other alloys which can comprise of a mixture of metals including, but not limited to, Co, Ni, Cu, Zn, and the like. In an aspect, the metallic trimmers 112 can include other materials shown in FIG. 5a, which plots density versus atomic number. In an aspect, Ti may be used, since it has an atomic number of 22 and a density of $4.5/cm^3$. In an aspect, titanium alloys may be used. While the composition and dimensions of the trimmers are in relation to the embodiments shown in FIGS. 4a-b, such compositions and dimensions can be applicable to trimmers of other embodiments discussed below as well.

In an embodiment, the driving mechanisms 114 can include high performance driving mechanisms 114 configured to rapidly move each trimmer 112. In an exemplary aspect, the driving mechanisms 114 are configured to have 2 g's of acceleration. The driving mechanism 114 can include, but are not limited to, linear motors or belt-driven actuators. In an aspect, motors provided by Automation, Inc. can be utilized as the driving mechanisms 114. The number of driving mechanisms 114 can correspond to the number of trimmers 112 utilized by the DTC 100. For example, in an exemplary embodiment, four linear motors 114 are associated with the four trimmers 112, with each motor 114 configured to move a trimmer 112, allowing for independent control of each trimmer 112. The ends of the driving mechanisms 114 (or the driving mechanism supporting structure or carriage) can be connected to one another, as shown in FIG. 4a-d.

The driving mechanisms 114 are connected to the trimmers 112 through connecting rods 116, with the connecting rod 116 being connected at an end of the trimmer 112. In an aspect, the DTC 100 includes a rail system 118 that supports the trimmers 112. The rail system 118 can be connected to a support frame 130. In an aspect, the rail system 118 provides a track/rail 119 on which the trimmers 112 can move. In an exemplary aspect, the trimmers 112 can include rail wheels 113 that engage the rails 119 of the rail system 118. In an exemplary aspect, the rails 119 can be curved, which allows the trimmers 112 to move in a pendulous arc to match the divergence of the ion therapy source (not shown).

In an aspect, the DTC 100 can also include a range shifter 120 (see FIGS. 4b-4d). The range shifter 120 is configured to be placed upstream of the patient to reduce the energy, and therefore the penetration depth, of the ion beam. For example, the range shifter 120 can be placed downstream of the ion therapy source and downstream of the spot scanning system discussed above. In an aspect, the range shifter 120 can provide 7.5 $g/cm^2$ of water-equivalent thickness located between the driving mechanisms 114 and the trimmers 112, enabling the range shifter 120 to be as close to the patient as possible. In an aspect, the integrated range shifter 120 is positioned such that the downstream face of the range shifter 120 is as close as possible to the patient without being downstream of the trimmers 112. In another aspect, the integrated range shifter 120 is positioned such that the downstream face of the range shifter 120 is as close as possible to the patient and also downstream of the trimmers 112. By mounting the range shifter 120 in such a position, the in-air penumbra at the plane of the trimmers 112 is minimized, reducing the required width and mass of the trimmers 112 required to block the spreading beam. Minimizing the mass of the trimmers 112 is an important aspect of the design for ensuring rapid dynamic motion of the trimmers 112. The range shifter 120 can also be removed when not needed, reducing the overall weight of the DTC 100 and easing installation of the DTC 100 onto the nozzle of an ion therapy system 150. The range shifter 120 can be supported by a carriage 122. The trimmers 112 can be associated below the range shifter 120 and carriage 122, along with the support rail 118. A support frame 130 can be utilized to contain the other mentioned elements of the DTC 100. While the embodiment of the DTC 100 discussed in reference to FIGS. 4a-d includes a range shifter 120, the DTC 100 does not need to have a range shifter 120.

In another aspect, the DTC 100 can supplement or replace the range shifter with one of many possible ridge filters (not shown). A ridge filter broadens the Bragg peaks used for treatment, reducing the number of beam energies required to treat a target. Different ridge filters broaden the Bragg peak to a different extent, and are appropriate for different patients. The use of different ridge filters can decrease treatment times and reduce the susceptibility of the delivered dose distributions to under-dose and overdose-causing interplay effects between the beam scanning pattern, trimmer motion pattern, and internal patient motion. A ridge filter can be placed by replacing the range shifter with a ridge filter, or replacing the range shifter with a combination of a smaller range shifter and a ridge filter.

In an aspect, the combination of the trimmers 112, the driving mechanisms 114, the connecting rods 116, the rail system 118, the range shifter 120, along with the support frame 130, form a protruding nose 102 for the DTC 100 that is small enough to position the trimmers 112 within several centimeters of the patient's skin (see FIG. 4d). The configuration allows the DTC 100 to be used even when treating sites such as the head and neck, even with the difficulties to access due to the presence of the patient's shoulders.

Referring back to FIGS. 4a-d, the DTC 100 is mounted downstream of the ion therapy source and spot scanning system, just upstream of the patient. In an exemplary aspect, the DTC 100 can be mounted on a nozzle of the spot scanning system. The driving mechanisms 114 are used to rapidly position the trimmers 112 during treatment such that the trimmers 112 track the edge of the target while the SS beam from the ion therapy source is scanned across the patient volume. The DTC 100 is designed such that the trimmers 112 can move rapidly enough to change positions while the ion beam is magnetically scanned across the target, with the trimmers 112 forming a rapidly changing frame that defines the sharp beam edges depending on the position of the ion beam. The configuration of the exemplary aspect minimizes the lateral spread of the beam by being close to the patient as possible.

In another embodiment of the present invention, illustrated in FIGS. 6a-b, a DTC 300 can contain a range modulation system 350. The range modulation system 350 enables the rapid modification of ion beam energies, reducing the time necessary to treat a target, without the need of a range shifter.

In an exemplary example of the embodiment, the DTC 300 includes a plurality of trimmers 312 connected to motors 314 by connecting rods 316. The DTC 300 can include a rail system 318 to support the trimmers 312 in a similar manner as discussed above. In an aspect, the range modulation system 350 can include of two linearly-traveling wedges 352 that face each other. In an aspect, the wedges 352 can be comprised of a low-atomic number material, including, but not limited to, lucite, graphite, beryllium, and the like, with a small proton scattering cross section.

Driving mechanisms 360 connected to the wedges 352 by wedge connectors 354 can control the wedges 352, and can be located in the space between the driving mechanisms 314 controlling the trimmers 312. When the wedges 352 are separated or brought closer together, the amount of range modulating material the ion beam passes through to reach the target is modified. The distance the driving mechanisms 360 are able to translate the wedges 352 of the range modulation system 350 dictates the range over which the ion beam ranges (penetrations) can be modified.

In an aspect, to ensure that the DTC 300 is small enough to be moved close to the patient in clinical practice, the DTC 300 can be oriented in a manner such that a collision with the patient would be avoided. In an aspect, the longest part of the DTC 300 can be oriented such that the axial plane of the DTC 300 is perpendicular to the patient's spinal cord, with the shorter part of the DTC 300 being oriented in the longitudinal direction parallel to the spinal cord of the patient. This strategy is especially important when treating head and neck cancers.

While not shown, a system controller, similar to those discussed above in relation to FIGS. 1-2, can be utilized in SS ion therapy systems that include the embodiments of the DTCs 100 and 300 illustrated in FIGS. 4a-4d and 6a-b as discussed above. In an aspect, irradiation, SS system, and position planning controllers (or modules) can be utilized to further control the operation of such DTCs 100, 300, including the range modulation system 350 of FIGS. 6a-b.

FIG. 7 illustrates another embodiment of a DTC 430 according to an aspect. FIG. 7 illustrates to driving mechanism 434 moving a trimmer 432 to a pre-defined position. The first axis of motion (the X axis) and second axis of motion (the Y axis) of the driving mechanism 434 correspond to two orthogonally superposed translation axes 438, 439 configured as a dual axis stage translation mechanism 434. In this aspect, the trimmer 432 is mounted on the first translation axis 438 of the driving mechanism 434 and is configured for making a translation motion along the first axis (i.e., parallel to the length of the first translation axis 438, shown by the double arrow). The first translation axis 438 is connected to the second translation axis 439 and is configured to translate over the first axis 438 along the second axis direction (parallel to the second translation axis 439, shown by the double arrow). Through this configuration, the trimmer 432 can be positioned to any pre-defined position in the plane defined by the two translation axes 438, 439, with the arrows indicating the direction of motions for the trimmer 432. In another aspect, the trimmer 432 can be mounted on the second translation axis 439.

In the aspect illustrated in FIG. 7, the pre-defined positions can be defined by defining a first parameter and a second parameter corresponding to the coordinate positions along the two translation axes. In such aspects, the position planning controller (not shown) is configured for defining, for one or more of said spot irradiations, corresponding pre-defined positions for positioning the trimmer 432. The same can be said for other embodiments of a DTC that include two translation axes. In an aspect, the position planning controller can utilize a display device to visualize the trimmer 432 together with an image of the target area (e.g., a two-dimensional x-ray image). On this image, the spot locations to be irradiated can also be visualized. A user can then use a user input device (e.g., a mouse) to move the trimmer 432 over the screen and position the trimmer at various places, including the spot positions, as well as move the spot positions themselves. A position of the trimmer 432 can be associated with a position of a spot to be irradiated through known means (e.g., selecting the trimmer 432 and spot positions with a mouse). In an aspect, the planning position controller can then calculate the coordinates for the two axes for each of the pre-defined positions selected by the user through the display device and user device.

Figure 8:
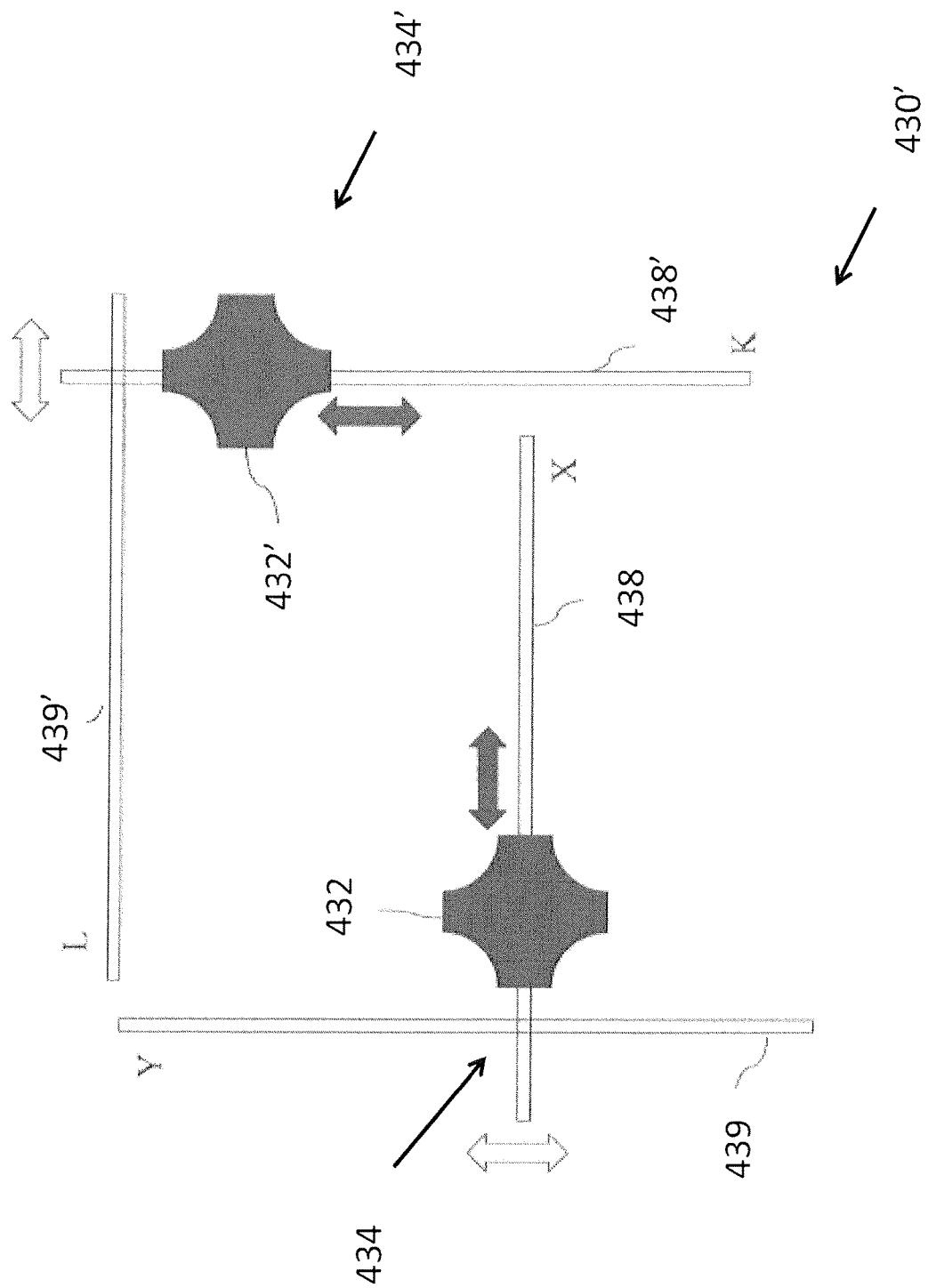
FIG. 8 is a schematic representation of a dynamic trimming collimator according to an aspect.

While FIG. 7 illustrates a DTC 430 utilizing only one trimmer 432, FIG. 8 illustrates a similar DTC 430 that utilizes two trimmers 432, 432' mounted each on their respective driving mechanism 434, 434'. As shown, the first driving mechanism 434 includes two axes of motion 438, 439 being two translation axes X, Y, which are configured for moving the first trimmer 432. This embodiment further comprises a second driving mechanism 434' with two axes of motion 438', 439', which are also two translation axes K, L and which are configured for moving a second trimmer 432'. In this embodiment, the driving mechanism 434, 434' are configured for moving the two trimmers 432, 432' in parallel planes.

Figure 9:
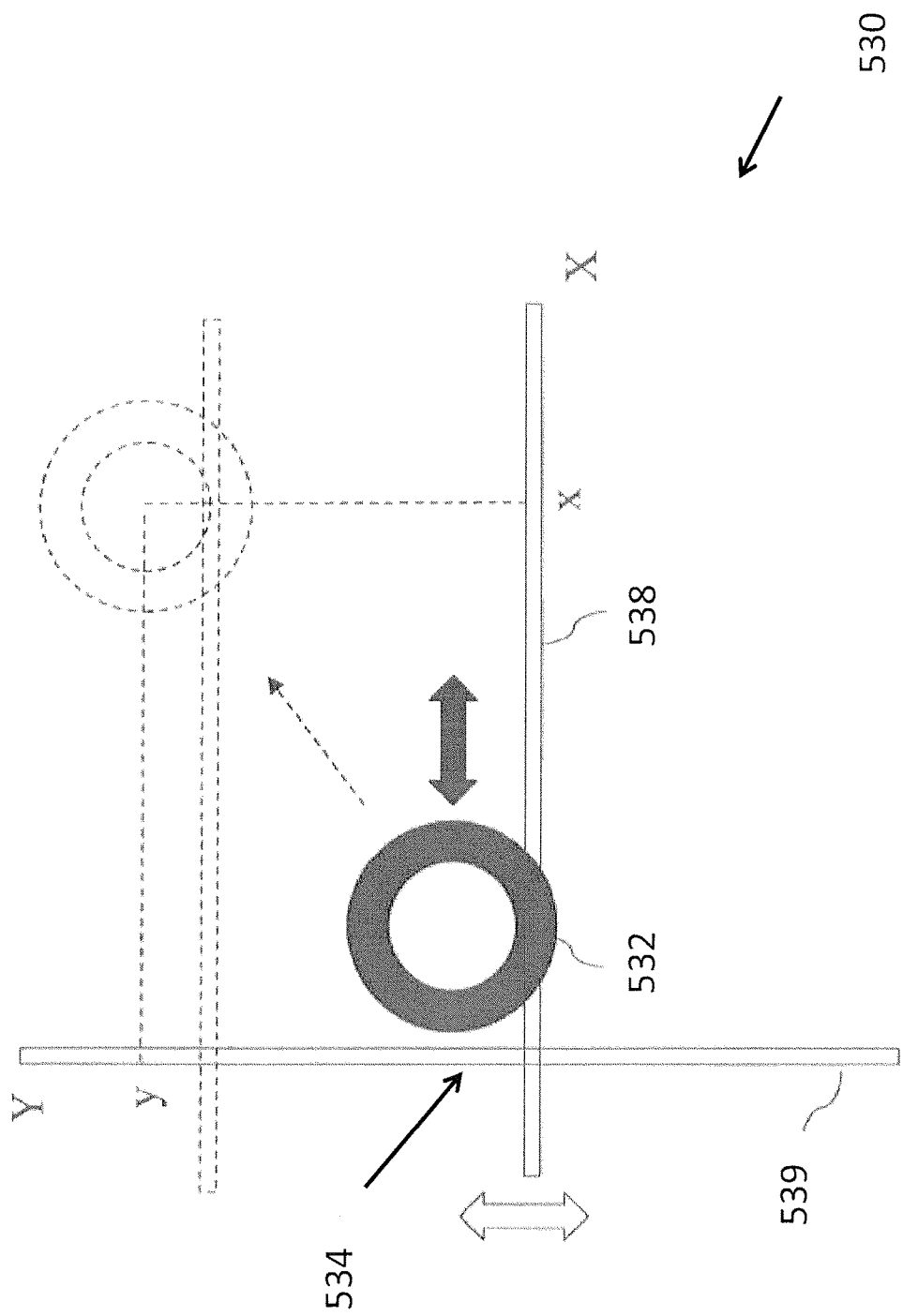
FIG. 9 is a schematic representation of a dynamic trimming collimator according to an aspect.

FIG. 9 illustrates another embodiment of the DTC 530 according to aspect of the present invention. The driving mechanism 534 is configured to move a circular trimmer 532 to a pre-defined position, with the first and second axis of motion (X, Y) correspond to two orthogonally superposed translation axes 538, 539 configured as a dual axis stage translation mechanism 534. The trimmer 532 is mounted on the first translation axis 538 and is configured for making a translation motion along the first axis X (i.e., parallel to the length of the first translation axis 538, shown by the double arrow). The first translation axis 538 is connected to the second translation axis 539 and is configured to translate over the first axis 538 along the second axis direction Y (parallel to the second translation axis 539, shown by the double arrow). Through this configuration, the trimmer 532 (and translation axes 538, 539) can be positioned to any pre-defined position, shown by the dashed lines, in the plane defined by the two translation axes 538, 539. In an aspect, an x parameter and a y parameter may be used to place the trimmer 532 at a location on the translation axes X, Y.

As discussed above, the trimmer 532 of the present embodiment is configured to have a circular shape. In an exemplary aspect, the trimmer 532 has four circular shaped sides. The circular outer shape defines the cutting edge for cutting part of the pencil beam (not shown), as well as the inner circular shape. However, a portion of the pencil beam can travel through the interior of the inner circular shape of the trimmer 532. By not having an interior portion of the trimmer 532, the weight of the trimmer 532 is reduced. In addition, irradiation can be done to spots that fall within the diameter of the inner circular shape of the trimmer 532.

Figure 10:
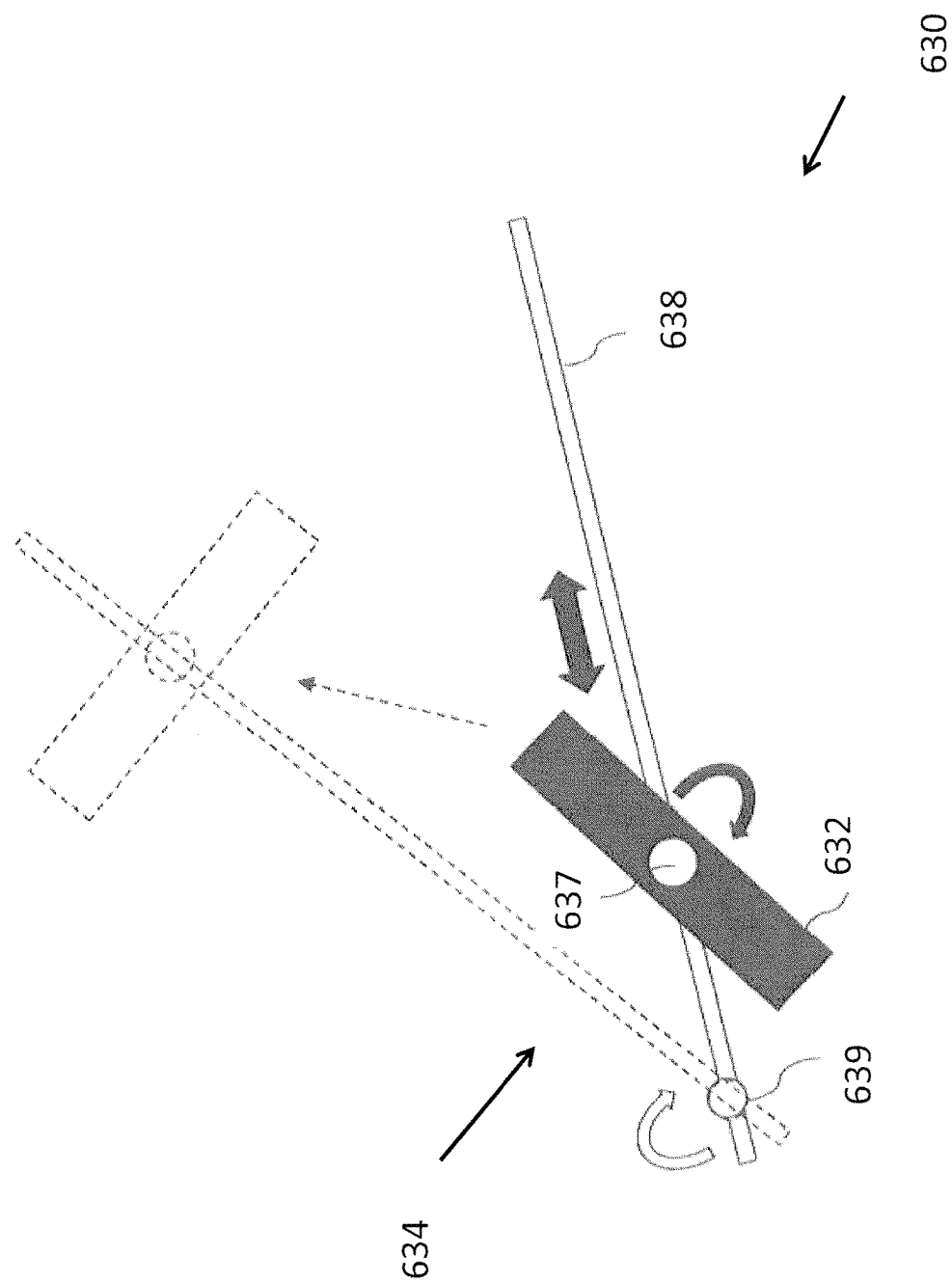
FIG. 10 is a schematic representation of a dynamic trimming collimator according to an aspect.

FIG. 10 illustrates another embodiment of the DTC 630 according to an aspect of the present invention, wherein the driving mechanism 634 includes a first axis of motion that is a translation axis 638 for translating the trimmer 632 and the second axis of motion is a rotation axis 639 for rotating the trimmer 632. The rotation axis 639 is essentially perpendicular to the translation axis 638 and the position of the trimmer 632 is defined within a first parameter corresponding to a coordinate position along the translation axis and a second parameter corresponding to a rotation angle with respect to the rotation axis 639. With such an embodiment, the trimmer 632 can be moved on a surface to any position to intercept the pencil beam during a spot irradiation. In the embodiment of FIG. 10, an additional rotation axis can be provided for rotating the trimmer 632 with respect to a rotation axis 637 crossing the trimmer 632.

Figure 11:
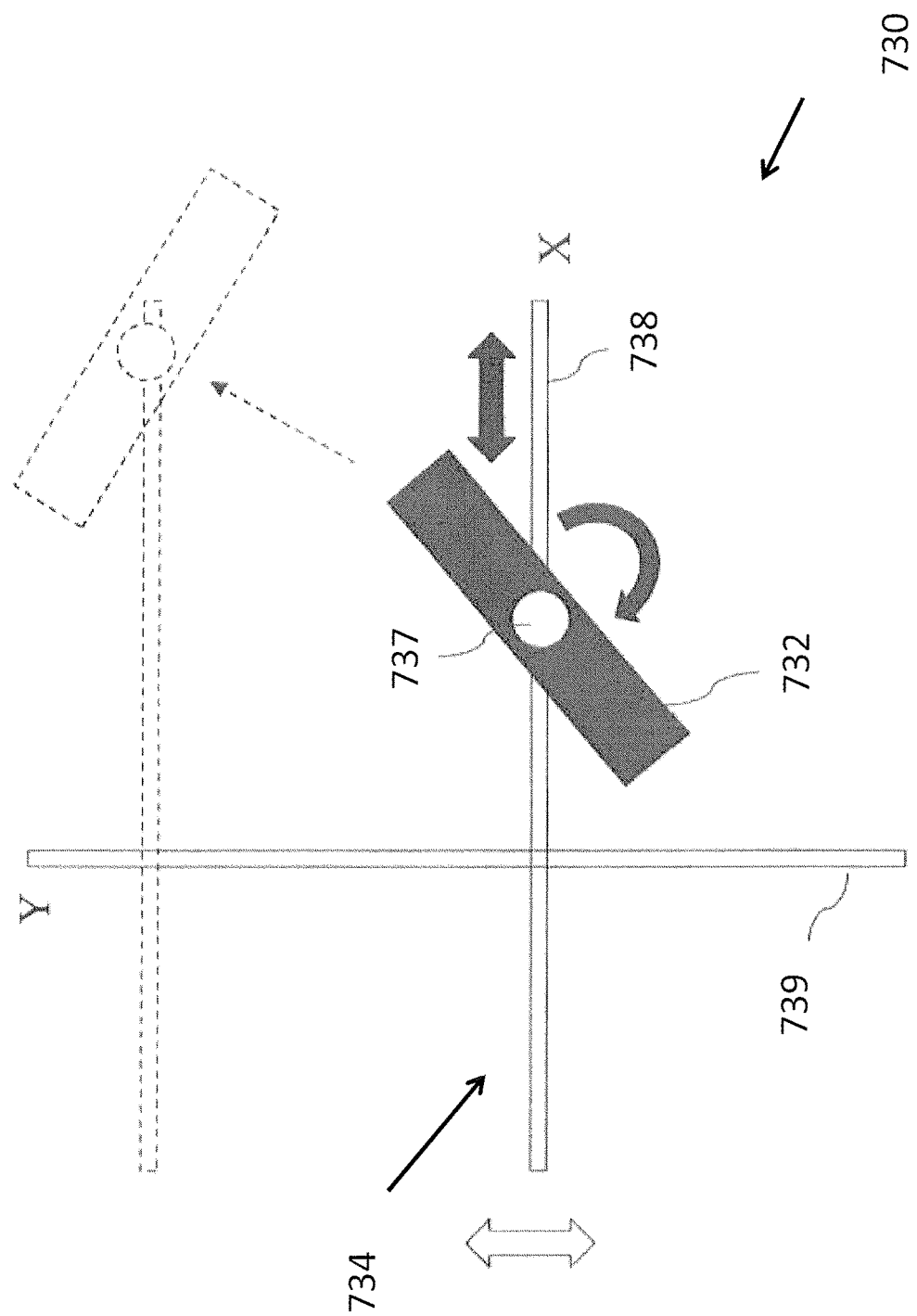
FIG. 11 is a schematic representation of a dynamic trimming collimator according to an aspect.
Figure 12:
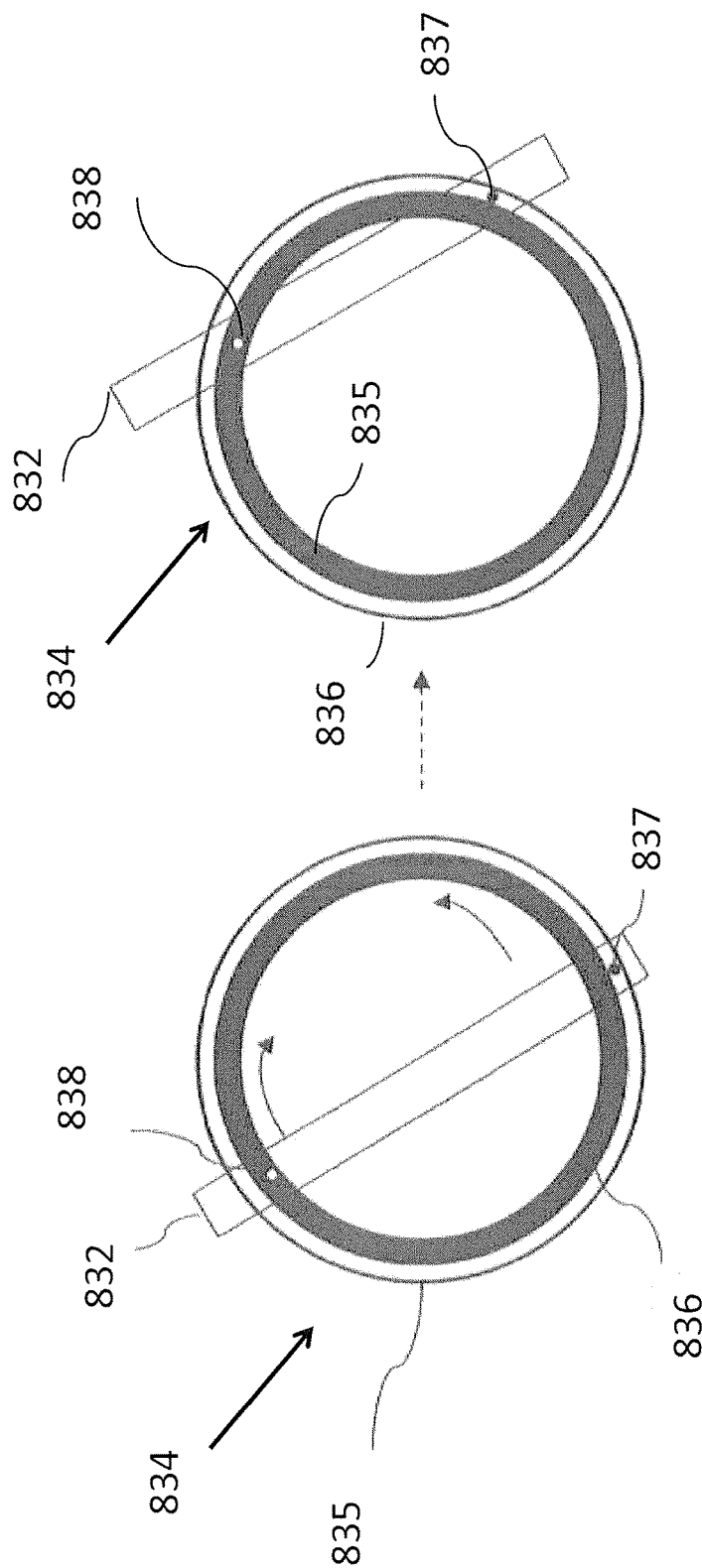
FIGS. 12a-b is a schematic representation of a dynamic trimming collimator according to an aspect.

FIG. 11 illustrates another embodiment of a DTC 730 according to an aspect of the present invention. The first axis and second axis (X, Y) of motion of the driving mechanism 734 correspond to two orthogonally superposed translation axes 738, 739 configured as a dual axis stage translation mechanism 734. In addition, the trimmer 732 includes a rotational axis 737. In this aspect, the trimmer 732 is configured for making translation motions along the first axis 738 and second translational axis 739, as well as rotation motions along the rotation axis 737 crossing the trimmer 732. Through this configuration, the trimmer 732 (and translation axes 738, 739 and rotational axis 737) can be positioned to any pre-defined position, shown by the dashed lines, in the plane defined by the two translation axes 738, 739 at a position with the plane defined by the rotational axis 737.

FIGS. 12a-b illustrates another further embodiment of a DTC 830 according to another aspect of the present invention. The trimmer 832 is moved by a rotatable driving mechanism 834 comprised of two rotatable concentric rings 835, 836. The trimmer 832 as shown is configured to have a rectangular shape and configured to slide on two points 837, 838 attached each to one of the rings 835, 836. When the rings 835, 836 rotate, the two points 837, 838 will rotate as well, resulting in the movement of the trimmer 832. FIG. 11a illustrates the initial position of the trimmer 832, while FIG. 11b shows another position of the trimmer 832 as the rotatable concentric rings 835, 836 have been rotated.

Figure 13:
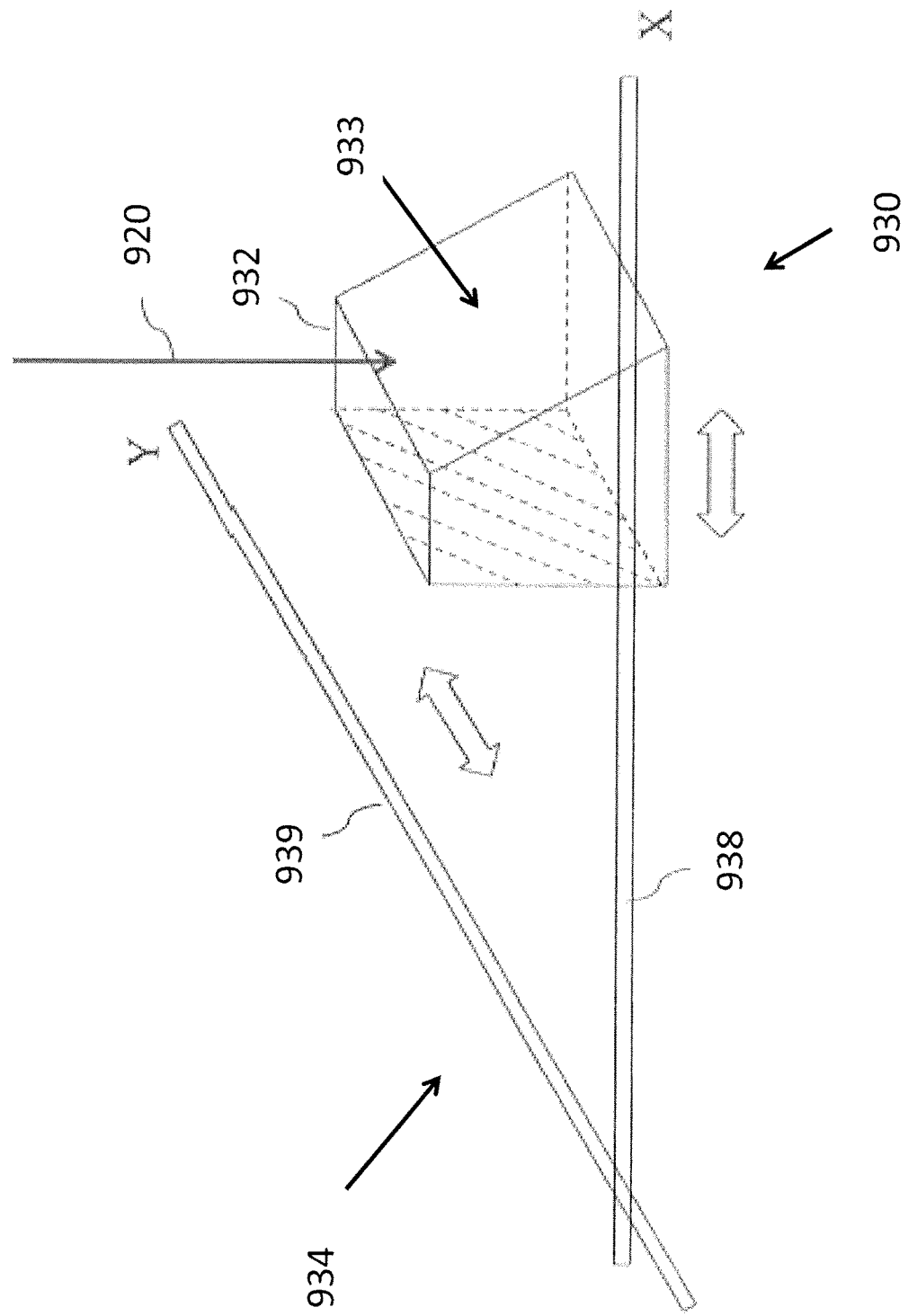
FIG. 13 is a schematic representation of a dynamic trimming collimator according to an aspect.

FIG. 13 illustrates an embodiment of a DTC 930 where not only the transverse phase beam can be changed by the trimmer 932, but also the longitudinal beam phase is adjustable as well. The trimmer 932 is mounted to a driving mechanism 934 with a first and second axis (X, Y) of motion that correspond to two orthogonally superposed translation axes 938, 939. As shown, the trimmer 932 is mounted on the first translation axis 938 of the driving mechanism 934 and is configured for making a translation motion along the first axis. The first translation axis 938 is connected to the second translation axis 939 and is configured to translate over the first axis 938 along the second axis direction. Through this configuration, the trimmer 932 can be positioned to any pre-defined position in the plane defined by the two translation axes 938, 939, with the arrows indicating the direction of motions for the trimmer 932.

As shown in FIG. 13, the thickness and shape of the trimmer 932 can be configured for changing the energy of the pencil beam 920. For this purpose, the trimmer 932 has a surface 933 that is inclined with respect to the pencil beam 920 such that depending on the relative position of the trimmer 932 with respect to the beam 920, the energy of the beam 920 is more or less reduced. In other words, the trimmer 932 comprises a plane that is inclined with respect to the X, Y plane of motion of the trimmer 932. In addition, the trimmer 932 also comprises a plane (indicated by dashed lines) that is perpendicular to the X, Y moving plane. Depending on the relative position of the pencil beam 920 and this plane, the pencil beam 920 can more or less be intercepted so as to change the lateral shape of the beam 920 and hence modify the transverse beam phase space. In other words, depending on the pre-defined position of the trimmer 932 defined by the coordinates on the motion axis 938, 939, either a longitudinal beam phase space or a transverse beam phase space can be changed.

In other embodiments, the DTC can utilize other range modulation systems. For example, in one aspect, the DTC can use a stairstep modulator, similar to that disclosed in EP20080730864. In another embodiment, the range modulation system can include a large water column similar to that shown in FIG. 3 of U.S. Pat. No. 8,129,701 B2. However, in another embodiment, a single water column can be utilized instead of the multiple shown in FIG. 3 of U.S. Pat. No. 8,129,701.

Testing Results

The ability to control the location of an ion beam using magnetic scanning is an advantageous property of ions that is not possible with photons. This is because photons carry no charge, therefore photon beams are controlled with mechanical collimation systems rather than magnetic fields. In an aspect, the SS method entails the magnetic and/or mechanical scanning of an ion beam over a 3-D Cartesian grid that covers the treatment volume. In an exemplary aspect, the position of a beam spot in depth is controlled by changing the energy of the proton pencil beam by inserting material in the beam, by controlling the beam energy with the proton accelerator, or a combination of both methods. In an aspect, the material can be placed in the beam-line somewhere between the accelerator and the gantry. Common materials may include beryllium and carbon. The number of ions that stop at each position in the target can be controlled by an ion accelerator and beam transport system (i.e., an ion therapy source and its components as discussed above), and can be initially determined by computer optimization (via a system controller) in a treatment planning process, discussed in more detail below.

Figure 5A:
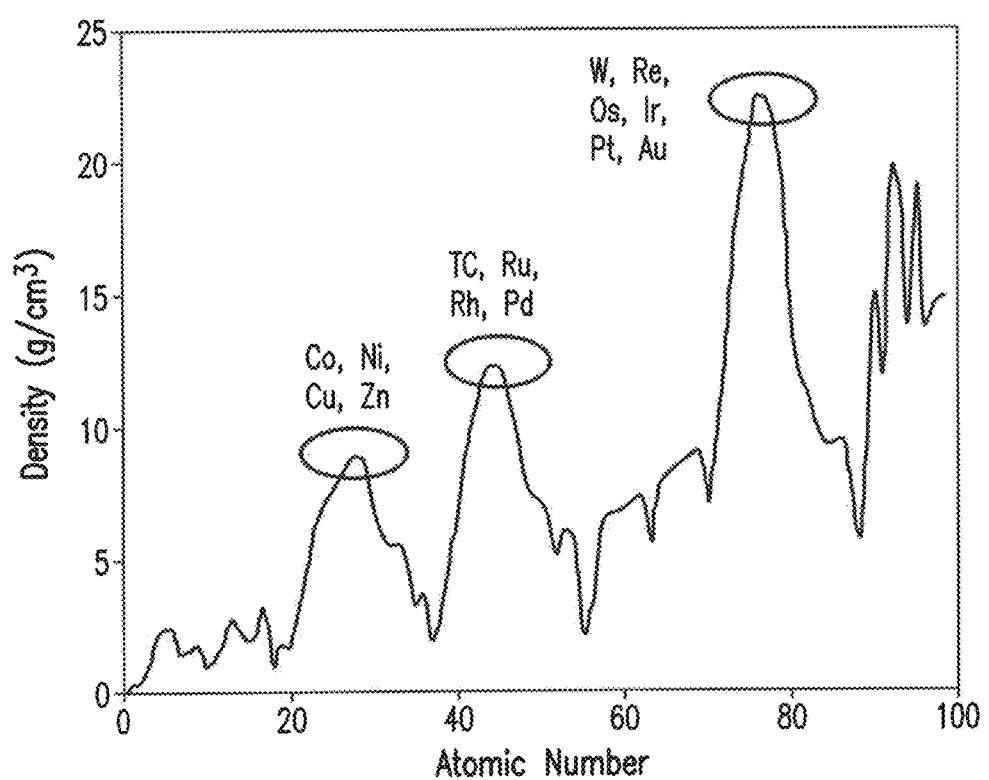
FIG. 5a is a graph of density versus atomic number of metals.
Figure 5B:
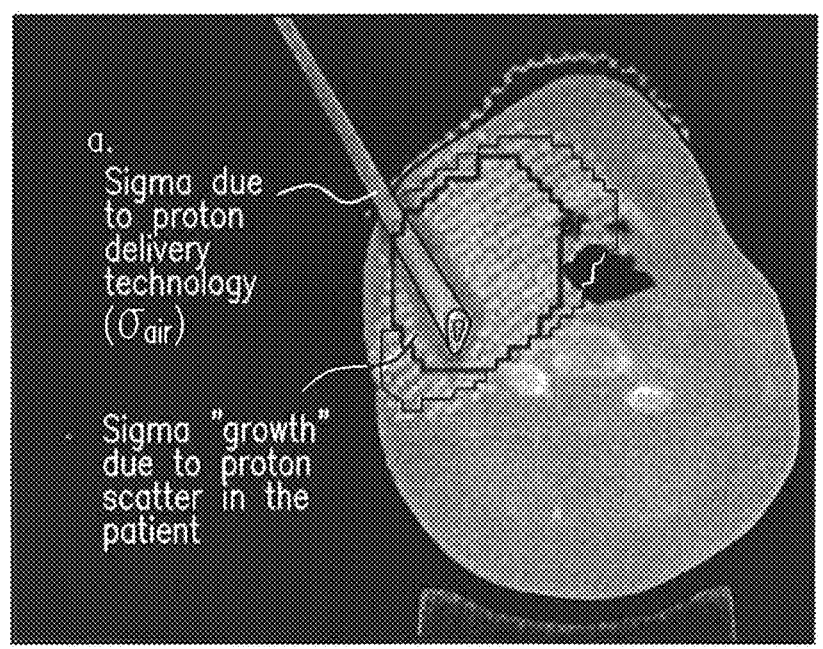
FIG. 5b is a dose distribution for a single proton beam spot according to an aspect of the present invention.
Figure 5C:
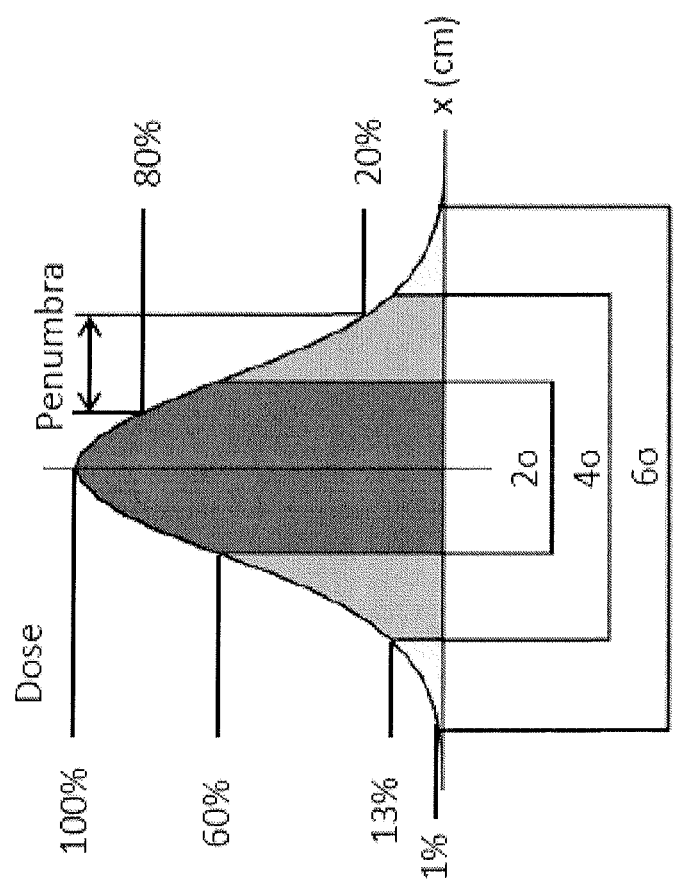
FIG. 5c is a graphical representation of a Gaussian lateral dose profile according to an aspect of the present invention.

A common measure of the lateral width of an ion beam is sigma ($\sigma$), which is the standard deviation of the beam's radiation dose profile on a line perpendicular to the direction of proton travel. A description of the $\sigma$-parameter is provided in FIG. 5c according to an aspect. FIG. 5b illustrates a dose distribution for a single proton beam spot in a head and neck cancer patient. The squares represent the locations of the Bragg peaks for all spots in the axial CAT scan slice shown. The value of the pencil beam sigma in air, $\sigma_{air}$, depends on the proton delivery technology, and the growth of $\sigma$ inside the patient is due to multiple Coulomb scattering, a physical process that cannot be modified. FIG. 5c illustrates a Gaussian lateral dose profile of a proton pencil beam in air, showing the definition of $\sigma$ and the 80%-20% penumbra.

A situation for which it is especially important that the radiation dose lateral to the target falls off sharply is intracranial (brain) stereotactic radiosurgery (SRS). In SRS, high radiation doses are delivered to benign lesions, such as acoustic neuromas, and malignant lesions, such as brain metastases, in a single high-dose irradiation session. The brain is highly susceptible to necrosis when small volumes of healthy tissue are exposed to high radiation doses. The dose that can be delivered to the lesion is then limited by the volume of the healthy tissue shell surrounding it, which is dependent upon the volume of the lesion. Ion SS radiosurgery of brain lesions can deliver a lower dose to the tissue shell surrounding the lesion, reducing the risk of healthy brain necrosis relative to photon-based radiosurgery techniques. Such an advantage for ion radiosurgery can only occur if the $\sigma$ of the pencil beams used for SS is below a certain threshold. In an aspect, $\sigma$ can be approximately 5 mm. However, $\sigma$ can vary in other aspects.

Figure 14:
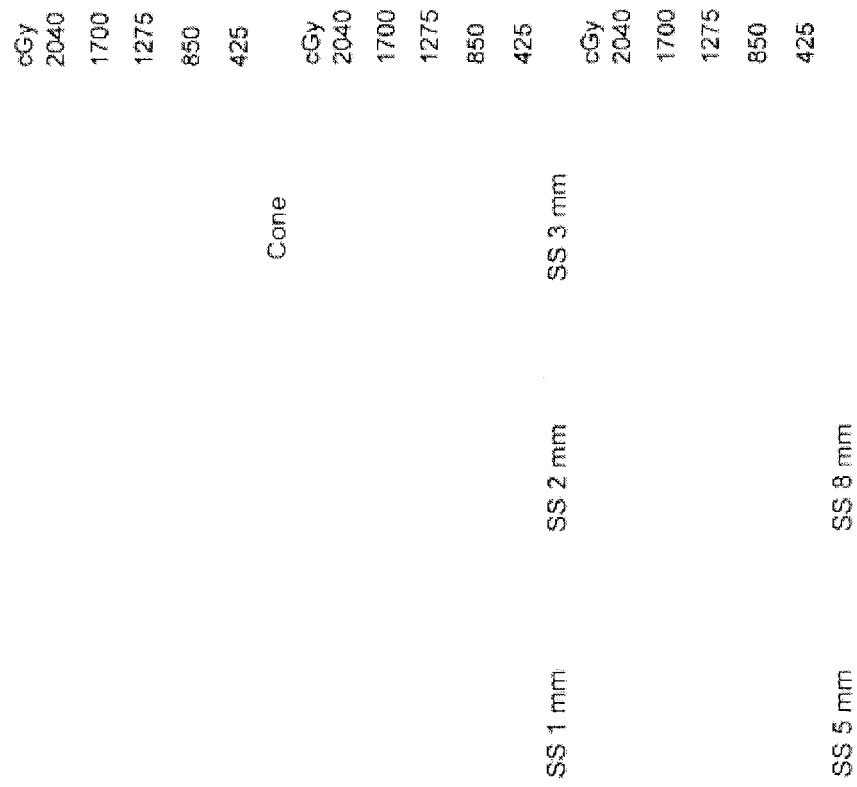
FIG. 14 illustrates radiation dose distributions according to an aspect of the present invention.
Figure 15:
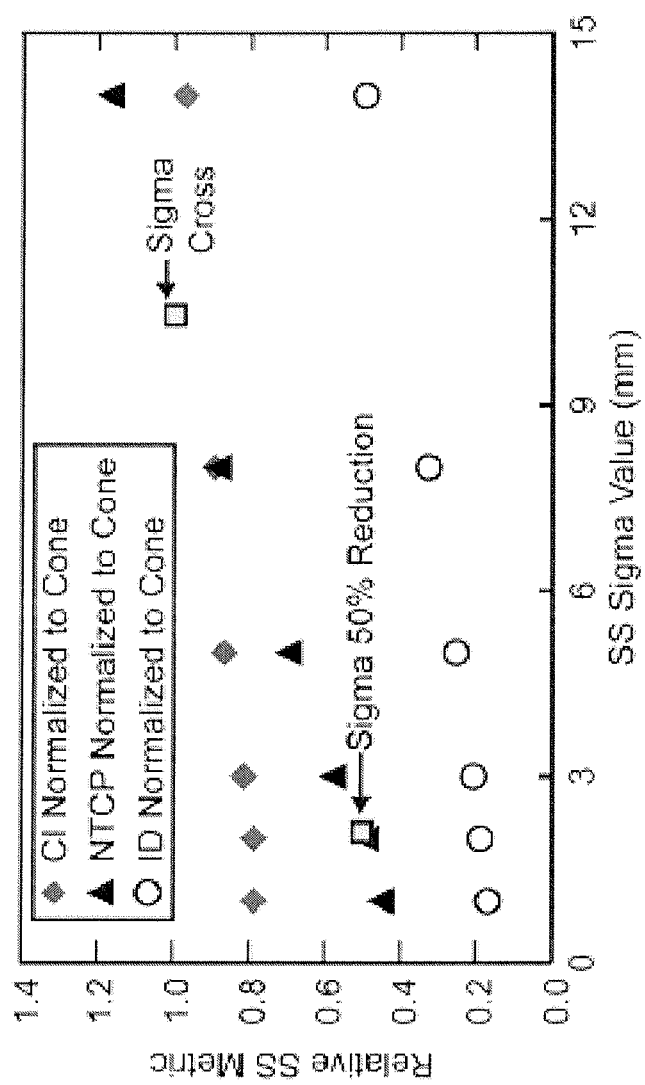
FIG. 15 is graphical representation of a plot of different sigmas according to an aspect of the present invention.

Examples of photon and proton SS radiosurgery treatment plans for a peripheral brain tumor represented by a clinical target volume (CTV) are shown in FIG. 14. Several different photon and proton SS plans with various radiation dose distributions are shown. The photon irradiation techniques shown are volumetric modulated arc therapy (VMAT) and cone-based radiosurgery, and the proton technique is spot scanning (SS).

The quality of the treatment plan degrades as the beam sigma increases, as shown for a single patient in FIG. 14.

Since the radiosurgery plans shown in FIG. 14 are for an intracranial brain tumor, the tissue for which the greatest hazard of complications exists is the healthy brain tissue. A normal tissue complication probability (NTCP) for brain tissue necrosis may be calculated for each plan in FIG. 14. For the proton therapy plans, the NTCP increases as the beam sigma increases and greater dose is delivered to the surrounding normal tissues. Since there is a range of NTCP values corresponding to the proton plans, we define "sigma-cross" as the proton pencil beam sigma which yields a proton plan with equal NTCP to that of the better of the two (VMAT or cone-based radiosurgery) photon plans. This value, along with sigma 50% reduction, which represents the beam sigma required to decrease the NTCP by 50%, are plotted in FIG. 15.

Figure 16:
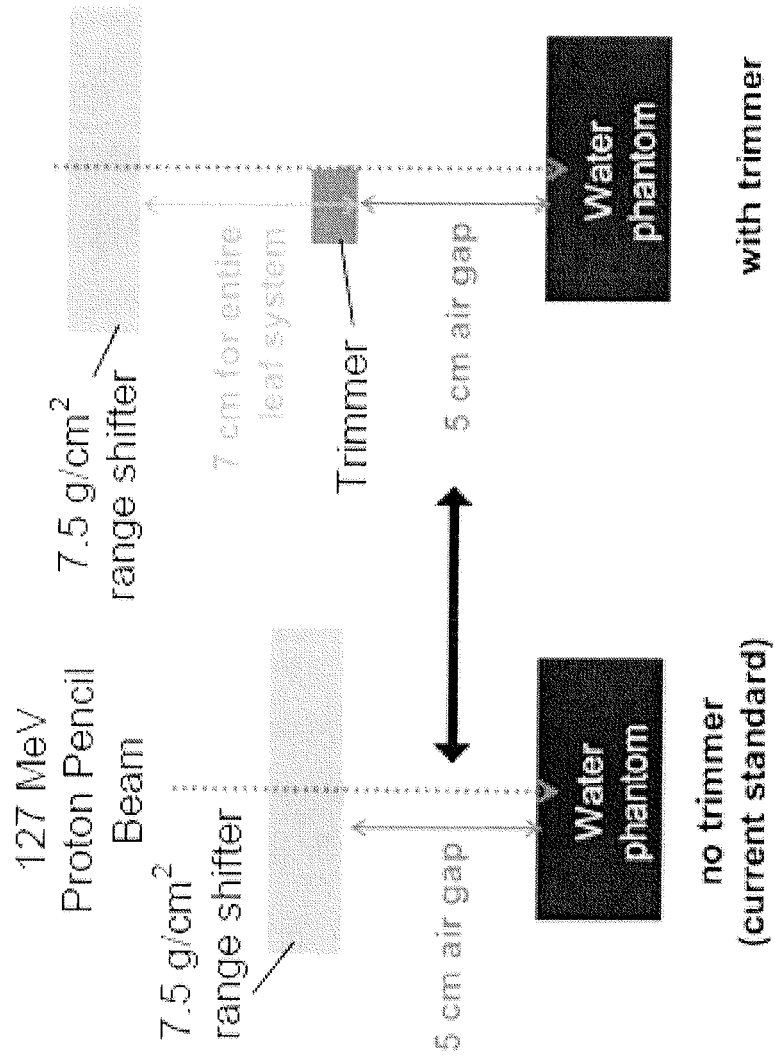
FIG. 16 is a graphical representation of a Monte Carlo simulation according to an aspect of the present invention.
Figure 18:
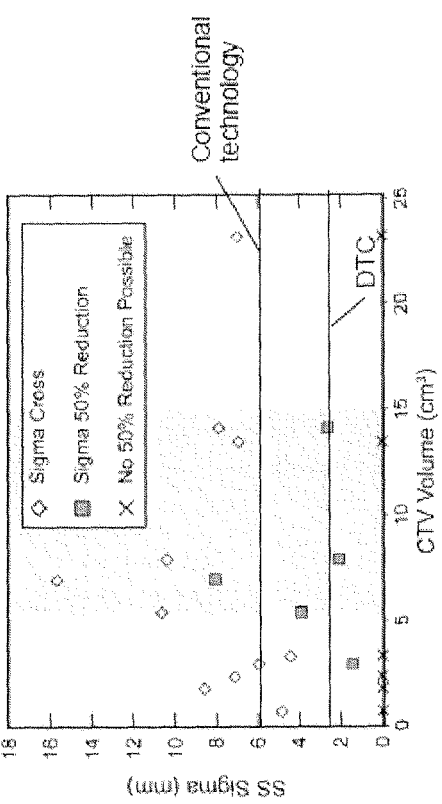
FIG. 18 is a graphical representation of NTCP values according to an aspect of the present invention.

In order to estimate effectiveness of DTSS at reducing proton pencil beam sigma for intracranial radiosurgery patients, proton beams at that surface of a phantom were simulated using Monte Carlo simulations with the MCNPX code for cases with and without a DTC in place, as shown in FIG. 16. For the conventional case of a proton beam with energy of 127 MeV, an initial sigma of 5 mm, a range shifter thickness of 7.5 g/cm$^2$, and a clinically realistic 5 cm air gap between the downstream range shifter face and the phantom (left side), the sigma in air at the phantom surface was 5.9 mm. With a DTC in place and a 5 cm air gap between the downstream trimmer and the phantom, the sigma in air at the phantom surface was 2.3 mm. These results are summarized in FIG. 17.

Sets of photon and proton SS treatment plans such as those in FIG. 14 were generated for 11 patients, and it was determined (FIG. 18) that 8 of 11 (73%) of the patients had NTCP values that could be improved relative to the photon plans when using commercially-available proton SS systems, which would have sigma values of approximately 5.9 mm for the tumor depths considered. If proton pencil beams with $\sigma_{air}$ values of 2.3 mm were used clinically, 100% of the 11 patients, shown in FIG. 18, considered would have a reduced healthy brain NTCP relative to photon radiosurgery techniques.

While improvements in $\sigma_{air}$ relative to conventional SS afforded by the DTC could be obtained using existing technology, existing technology consists of either patient-specific brass apertures (i.e., pieces of brass with openings cut out to match the shape of the tumor) or multi-leaf collimators. Since a given brass aperture is shaped only to match the tumor extent for a single plane in the tumor, apertures are not capable of sharpening the 3-dimensional dose distribution to the extent a multi-leaf collimator or the DTC could. In addition, brass apertures need to be manufactured for each patient, and for each beam with which the patient is treated, adding substantial cost of around $500 per custom aperture to the delivery process. Brass apertures also require a construction time, imposing a lower-bound on the time required to plan, prepare for, and deliver a patient's treatment. This is an especially important limitation for SRS, as it is typical for a patient to be treated on the same day their plan is generated with photon SRS. Removing this benefit imposes an impediment to the widespread adoption of ion SRS.

MLCs have been proposed as a means to improve SS penumbra. Bues et al (2005) demonstrated that an MLC can be effective at sharpening SS penumbra for low energy proton beams, but found that diminishing returns occurred as the proton beam energy increased. As shown in Table 1, the MLC substantially reduced the 80%-20% penumbra at the depth of the Bragg peak for beam energies of 72 MeV and 118 MeV, but increased the penumbra for the 174 MeV beam. This is because the 20.5 cm range of the 174 MeV proton beam was sufficiently high that multiple Coulomb scattering interactions inside the medium dominated over any improvements in $\sigma_{air}$ provided by the MLC. For shallower depths, multiple Coulomb scattering interactions did not dominate, enabling substantial improvements in penumbra with the use of the MLC. The effective $\sigma_{air}$ value in Table 1 was calculated by scaling the $\sigma_{air}$ value before the MLC by the ratio of the penumbra with-to-without the MLC. Since there is nothing that can be done to prevent multiple Coulomb scattering interactions from occurring between ion beams and patient tissue (FIG. 5b), the advantages of the DTC relative to the collimator-free case are similar to those of the MLC in terms of ability to shape a dose distribution.

TABLE 1

Penumbra at the location of the Bragg peak for proton beams without and with an MLC.[1] The penumbra values are taken from a 7 × 7 pattern of equally-weighted beam spots. The distal ends of the MLC leaves are assumed to be 5 cm from the patient surface. Penumbra values represent the distance between the 80%-20% isodose lines.

| Energy (MeV) | Range (cm) | $\sigma_{air}$ before MLC (mm) | Penumbra w/o MLC (mm) | Penumbra w/MLC (mm) | Effective $\sigma_{air}$ from MLC (mm) |
|---|---|---|---|---|---|
| 72 | 4.3 | 11.0 | 13.0 | 3.0 | 2.5 |
| 118 | 10.3 | 7.2 | 9.0 | 5.0 | 4.0 |
| 174 | 20.5 | 5.5 | 8.0 | 9.0 | 6.2 |

The advantage of utilizing a DTC over a MLC is that the ratio of usable beam area to total area of the face of the DTC is far higher than that of an MLC. Since the penumbra grows geometrically with distance to the patient surface, it is critical that the DTC or MLC is located as close to the patient as possible. The MLC leaves must go somewhere when retracted out of the radiation field, and the housing around an MLC tends to be bulky. This makes MLCs difficult to move to within 10 cm of the patient surface when treating the head and neck region.

Figure 20:
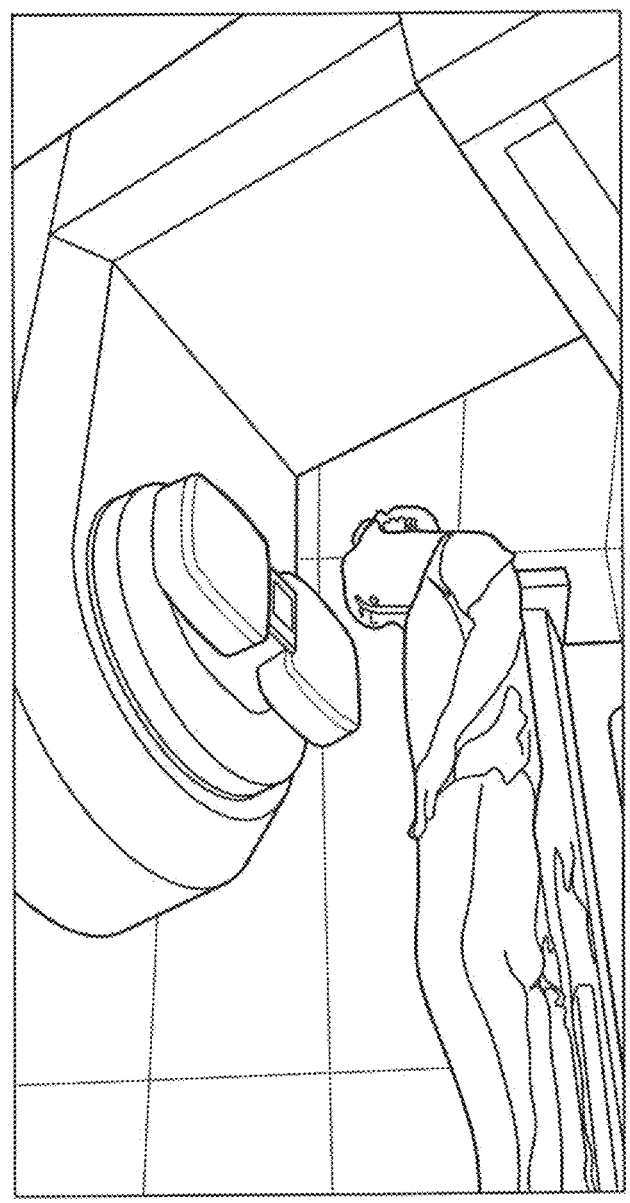
FIG. 20 is an image of the Siemens ModuLeaf.

Two of the smallest available MLCs are the Siemens ModuLeaf and the Radionics MMLC, shown in FIGS. 19a-b, respectively, which have physical field sizes of 7.8 cm×6.5 cm and 6.9 cm×5.4 cm, respectively. The ModuLeaf is also shown in FIG. 20. As shown in FIG. 19a, the percentage of nozzle area through which the proton beam can pass is about 46% for the DTC, which has a physical field size of 15 cm×15 cm, and only 7% for the Siemens ModuLeaf. Thus, even if an existing MLC can be placed close to the patient surface, four junctioned fields (i.e., multiple small fields combined to make one larger field) from the MLCs would be needed to cover the same area as a single DTC field. Although junctioning fields are typically not necessary for intracranial lesions treated with the ModuLeaf, as shown in FIG. 20, larger fields that would require junctioning are expected for many head and neck, esophageal, lung, craniospinal, sarcoma, and liver cancer patients. In addition, commercially available MLCs are optimized for photon therapy rather than proton therapy, which is an important consideration since beam modifying devices for proton therapy are subjected to substantially higher neutron doses than those used in photon therapy. The high neutron doses necessitate the use of electronics that are less sensitive to neutron damage.

There are two major enabling principles behind DTC-based DTSS. First, spot scanning dose distributions are only improved by collimation systems when relatively low-energy ion beams are used, which have energies <160 MeV at the patient surface for proton beams. This is because the penumbra at deeper depths from higher energy beams is largely dominated by scatter in the patient. This fact allows the radiological thickness of the trimmers to be slightly greater than that of the range of a low energy proton beam, and lightweight compared to traditional collimators, such as the multi-leaf collimators (MLC) used in photon and ion therapy. Second, with SS, a collimator is necessary at the edge of the target only at the times when the beam is near the edge of the target, and the trimmers can be in motion when the beam is elsewhere, as long as the trimmer motion does not interfere with the scanned beam motion.

Modeling of Beamlet Dose Distributions

Figure 21A:
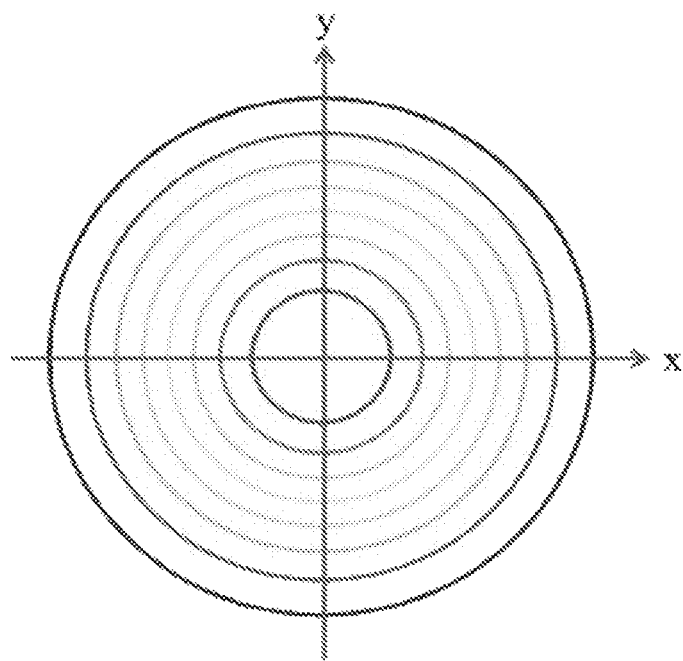
FIG. 21a is a Beam's eye view of a proton lateral dose distribution according to an aspect of the present invention.
Figure 21B:
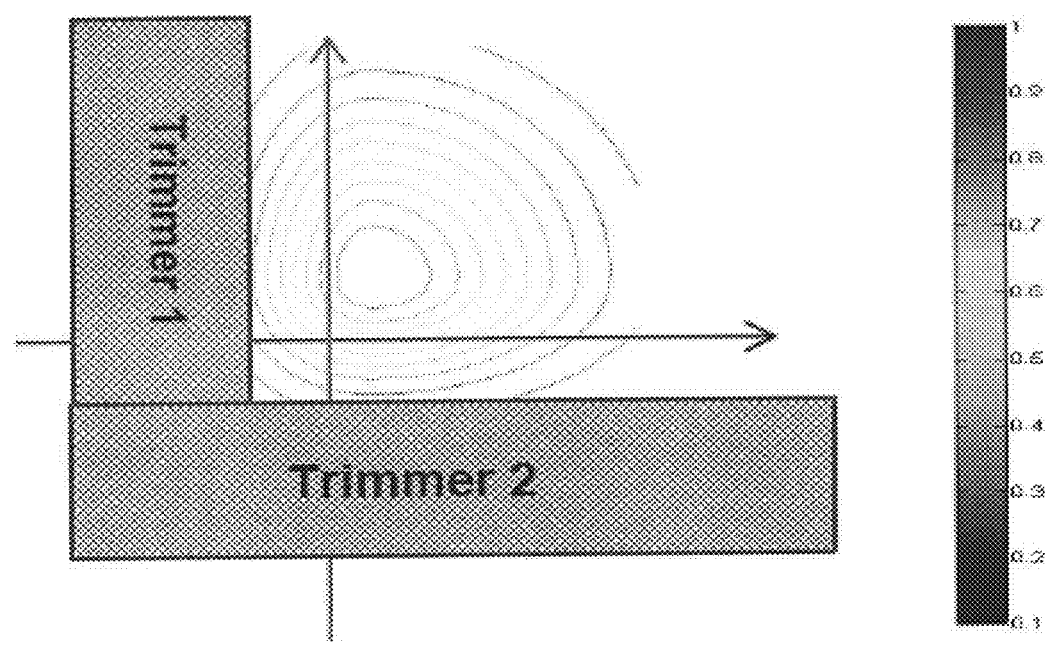
FIG. 21b is a Beam's eye view of a proton lateral dose distribution with trimmers according to an aspect of the present invention.
Figure 21C:
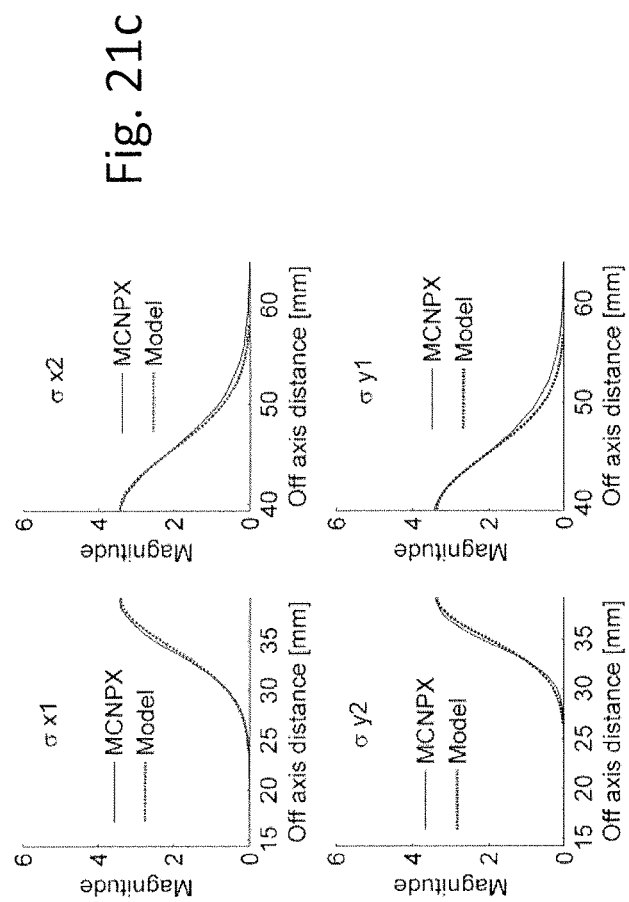
FIG. 21c is a graphical representation of the lateral distribution of an asymmetric trimmed beamlet using Gaussian parameters according to an aspect.

In an aspect, after interacting with the trimmer blades, incoming symmetric proton beamlets (shown in FIG. 21a) can become asymmetric and laterally shift in the beam's eye view, as illustrated in FIG. 21b. In an exemplary aspect, the lateral distribution of an asymmetric trimmed beamlet can still be described using Gaussian parameters, similar to the untrimmed beamlet. This is accomplished by fitting Gaussian functions along each of the four primary lateral axes of the trimmed beamlet, namely $X_1$, $X_2$, $Y_1$, and $Y_2$, as shown in FIG. 21c. With this approach, the lateral profile can then be modeled as follows:

$$O(x, y, z) = A(z)\exp\left\{-\left[H(x-\mu_x(z))\frac{(x-\mu_x(z))^2}{2\sigma_{x1}^2(z)} + H(\mu_x(z)-x)\frac{(x-\mu_x(z))^2}{2\sigma_{x2}^2(z)} + H(y-\mu_y(z))\frac{(y-\mu_y(z))^2}{2\sigma_{y1}^2(z)} + H(\mu_y(z)-y)\frac{(y-\mu_y(z))^2}{2\sigma_{y2}^2(z)}\right]\right\}$$

where $\mu_x^{(z)}$, and $\mu_y^{(z)}$ are the positions of maximum dose in the plane of interest and $\sigma_{x1}^{(z)}$, $\sigma_{x2}^{(z)}$, $\sigma_{y1}^{(z)}$, $\sigma_{y2}^{(z)}$ are the sigma values for the four half-Gaussians along each primary axes, centered on ($\mu_x^{(z)}$, $\mu_y^{(z)}$) at depth z. The Heaviside step function H( . . . ) limits each exponential term to the corresponding half-axis centered at ($\mu_x^{(z)}$, $\mu_y^{(z)}$). Multiplication by a numerically determined normalization factor A(z) ensures that $\iint_{-\infty}^{\infty} O(x,y,z) dx\, dy = 1$ for all z. Such a method can be applied to any asymmetric beamlet, not only those resulting from collimation.

Figure 22:
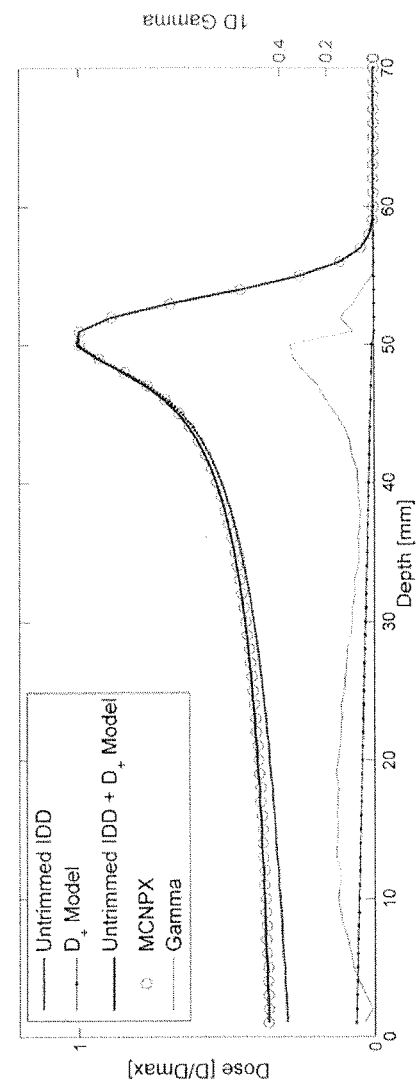
FIG. 22 is a graph comparison of untrimmed and trimmed IDD comparison at an energy of 128 MeV with trimmers positioned at [X1=0, X2=2] cm and [Y1+0, Y2=2] cm from the central axis of an untrimmed beamlet. A 1D Gamma evaluation is also shown in the plots with a 2%/1 mm criteria.

In an aspect, after interacting with the trimmer blades, the integral depth dose (IDD) curve of the trimmed beamlet changes from that of an untrimmed beamlet, as illustrated in FIG. 22. By applying a depth dependent correction function, the trimmed beamlet IDD curve can be generated from the untrimmed beamlet IDD. One such correction function takes the form of the equation below:

$$D_+(z,R)=D_+(0)\cdot(C\cdot z+1)$$

where $D_+(z,R)$ represents the depth dependent correction applied to the untrimmed IDD to generate a trimmed IDD, $D_+(0)$ is the increase in entrance dose (%) of the trimmed IDD compared to the untrimmed IDD at the surface, and C is a constant parameter that is a function of energy determining the depth dependence of the correction. The equation below describes how the trimmed IDD represented by $D_T(z,R)$ may be obtained by addition of the untrimmed integral depth dose curve $D(z,R)$ and the correction described above:

$$D_T(z,R)=D(z,R)+D_+(z,R)$$

Determining Time-Dependent Trimmer Positions for DTSS Delivery

In an aspect, distributing spots in a grid or hexagonal pattern across the target volume and then defining trimmer positions later can be used for placing beam spots. Any DTSS spot placement technique will still produce dose distributions that are superior to those that can be delivered with conventional SS.

In another aspect, trimmed spot peak tracing (TSPT) produces superior dose distributions to those achievable with grid or hexagonal spot placement patterns. TSPT is based on the logical conjecture that maximizing the conformity of the dose to the target volume requires that the dose maxima of trimmed spots are positioned on the edge of the target volume. Due to proton scatter off the trimmer and in the target medium, the point of maximum dose in the beam's eye view of a trimmed spot does not occur on the ray along which the scanning magnets are directing the pencil beam upstream of the trimmer. Positioning the point of maximum dose of a trimmed beam spot thus requires that the scanning magnets and trimmers work together.

Figure 17:
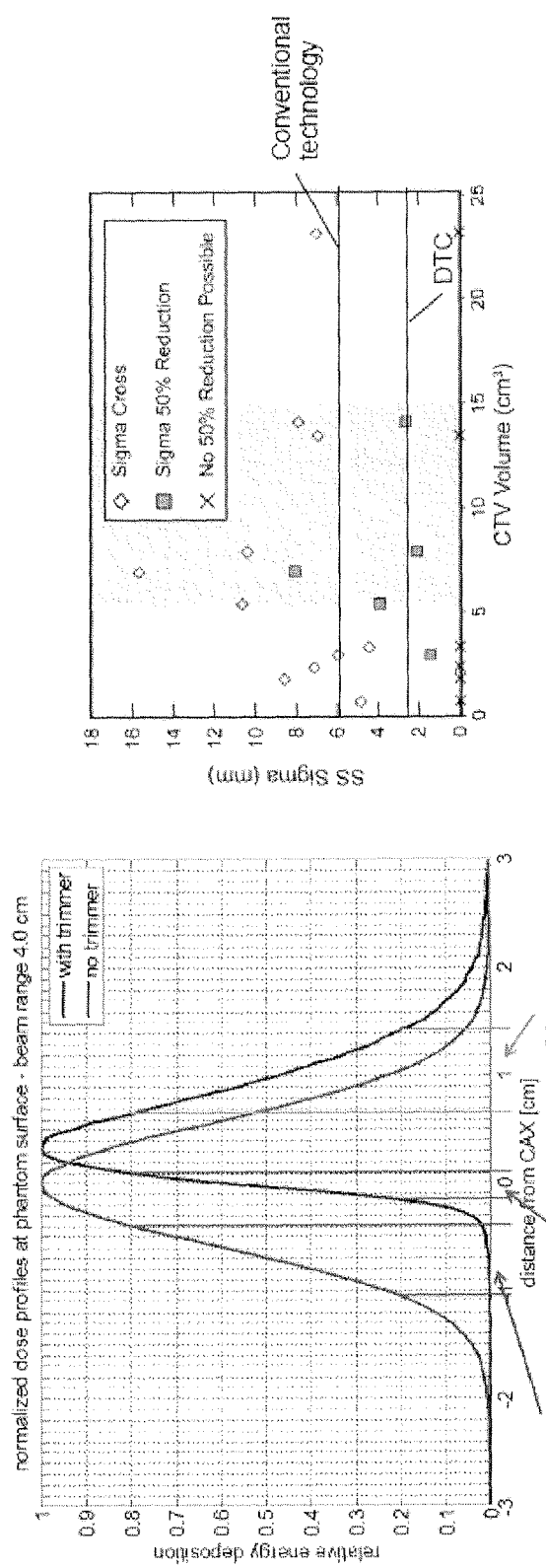
FIG. 17 is a graphical representation of proton pencil beams from the Monte Carlo simulation defined in FIG. 16.
Figure 23:
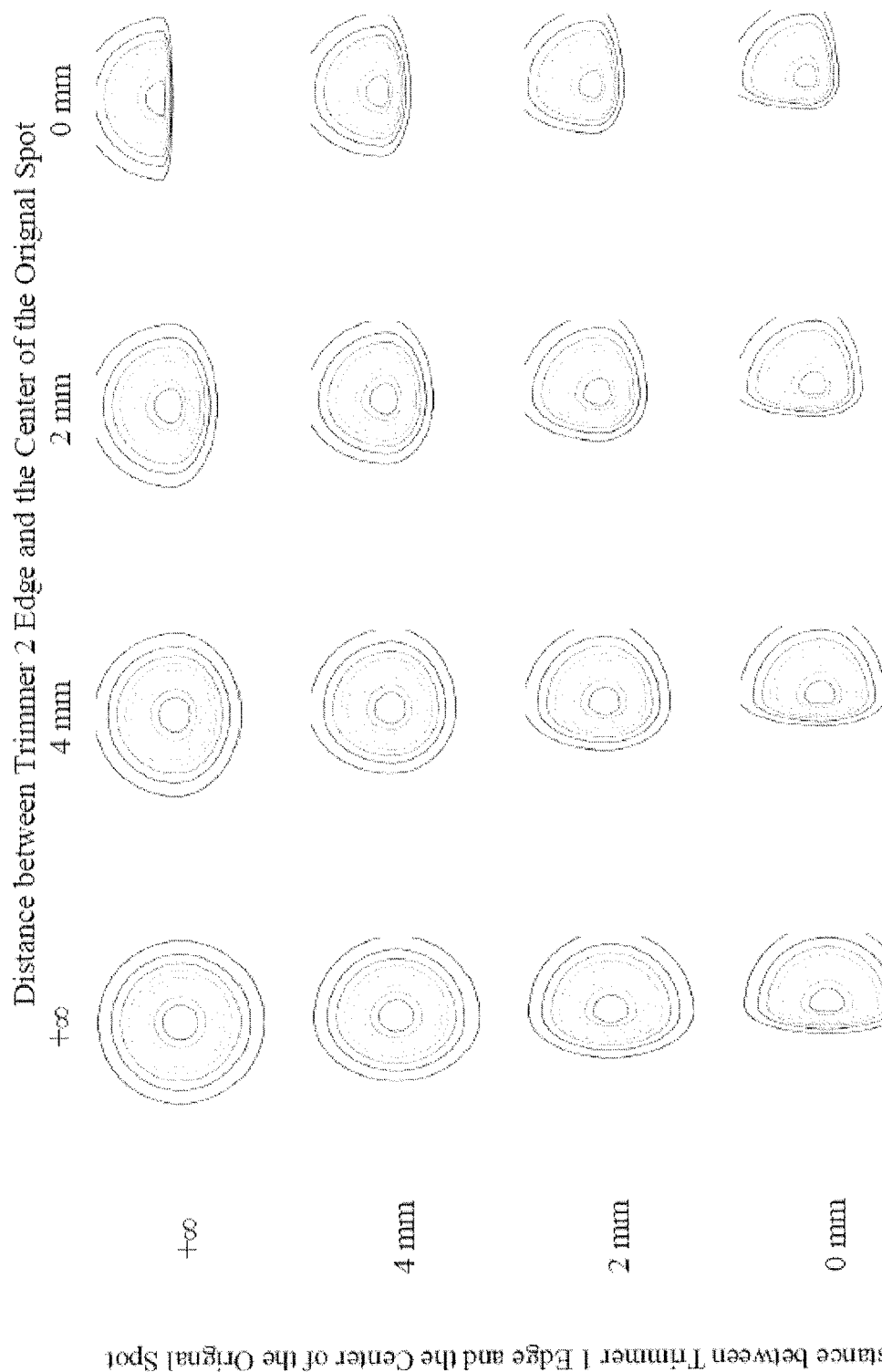
FIG. 23 is an example of a trimmed pencil beam library according to an aspect of the present invention.

The following is a description of an implementation of the TSPT method according to an aspect. According to an exemplary aspect, as shown in FIGS. 16-17, a single trimmer can reduce the value of $\sigma_{air}$ on one side of the trimmer for a proton pencil beam spot from 5.9 mm to 2.3 mm. The location of the point of maximum dose of the beam spot is also shifted away from the trimmer. FIGS. 21a-b show that an orthogonal set of trimmers can reduce the values of $\sigma_{air}$ on both dimensions of a proton pencil beam spot as a two-dimensional Gaussian. Similarly, trimmers on three or four sides of a pencil beam can reduce the value of $\sigma_{air}$ on each side where a trimmer is placed, and shift the position of the spot peak. By positioning the trimmers at different distances from the center of the incoming spot, the location of the point of maximum dose and 2-D $\sigma_{air}$ value can be varied. According to an aspect, a trimmed pencil beam (i.e., a beam that has been shaped by intercepting trimmers) (TPB) library can be calculated for varying trimmer position combinations, as shown in FIG. 23. These TPBs represent various trimmer positions at various distances from the central axis of the pencil beam of ions to achieve the desired dose distribution.

Figure 24:
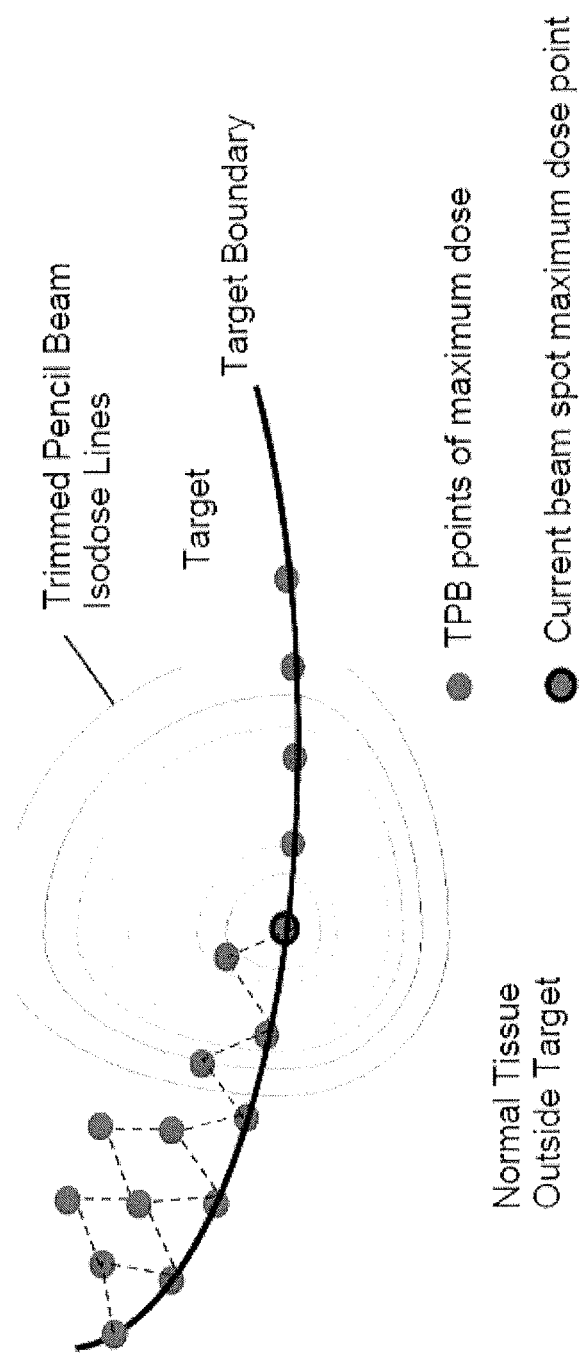
FIG. 24 is a schematic representation of a trimmed spot peak tracing scheme according to an aspect of the present invention.

Once the TPB library exists, a method for selecting the appropriate TPB maximum dose location, and, therefore, trimmer configuration, for a given point in the target volume can be defined. FIG. 24 shows the target boundary at an arbitrary energy layer in the beam's eye view. The desired TPB maximum dose points can be positioned at equidistant points on the target boundary, which may, for example, be 5 mm apart. Following the placement of TBP dose maxima on the target boundary, the remaining beam spots can be placed throughout the target volume in a lattice pattern such as that shown in FIG. 24. Alternatively, a fixed spot grid of spot positions may be used with a square, hexagonal, or other pattern, the nearest neighbor spot may be assigned to the target boundary. In such a situation, if scanning magnets are always configured to position the nearest spots to the target border outside the target, a trimmer configuration will exist that could position the point of maximum dose of the TPB closer to or on the target boundary. The desired TPB maximum dose point location is on the target boundary.

At each desired TPB maximum dose location, the TSPT algorithm searches the library of i=1, . . . , NTPB trimmed spot kernels for the pencil beam energy, and selects the TPB trimmer configuration that satisfies a search criterion such as:

$$\min_i TE_i \quad (1)$$

where $$TE_i = \frac{\text{Total energy deposited inside target from } TPB\ i}{\text{Total energy deposited outside target from } TPB\ i} \quad (2)$$

Another possible TPB search criterion is $$\min_i MD_i \quad (3)$$

where $$MD_i = \frac{\text{Mean dose to target areas above } x\ \%\ \text{isodose line}}{\text{Mean dose to normal tissue area above } y\ \%\ \text{isodose line}}. \quad (4)$$

Alternatively, a weighted combination of search TPB criteria can be used as a weighted sum:

$$C_i = (1-\omega)TE_i + \omega \cdot MD_i, \quad (5)$$

where w is a scalar weighting factor valued between 0 and 1.

A TPB placement strategy according to another aspect is to assign a large number of initial spots with very small inter-spot distance and generate a treatment plan by optimizing the spot weight, which is proportional to the number of ions, to deliver to each spot. In an iterative process, some fraction of the spots with low weights can then be removed, reducing the number of spots required for delivery. If any trimmed spot on the target boundary cannot be created by realistic trimmer positions, it would be replaced with the one with the closest spot shape.

According to an aspect, determining the position of each of the four trimmers, as shown in FIGS. 4a-d, necessitates an algorithm that accounts for spot position, spot size, target shape, and the fraction of total spot energy, $\epsilon$, that the user is willing to accept being delivered to normal tissue outside of the target in the plane being treated. In an aspect, such an algorithm can be implemented by DTSS software, as discussed below.

If $\epsilon=0$, then the trimmers will not allow any spot energy to be deposited outside of the target. This would not be desirable for targets with curved edges (non-rectangles) because the trimmers may have to change position between each spot, dramatically increasing delivery time relative to the case without trimmers. In addition, not allowing any spot energy to fall outside the target could result in trimmer positioning patterns that are too conservative to allow certain regions in the target from receiving a dose, resulting in underdosage of the target. To avoid these problems, options to allow a non-zero fraction of energy from a given beam spot to fall outside the target can be provided. Specifically, the algorithm maximizes ET, the spot energy deposited in the target, under the constraint that ENT, the energy deposited in the normal tissue, should be less than or equal to $\epsilon$ times $E_{tot}$, the total energy deposited by the spot.

Figure 25:
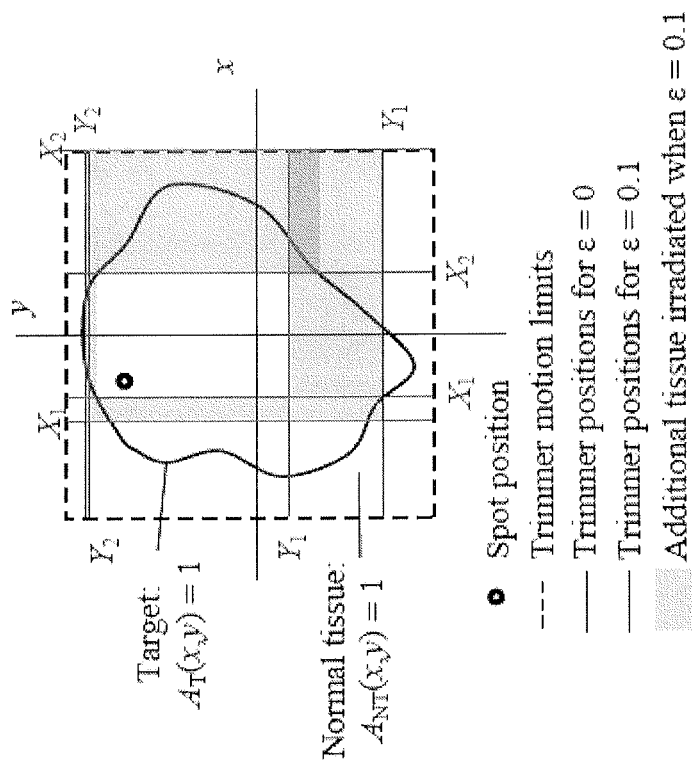
FIG. 25 is a representative schematic of trimmer positions in the beam's eye view according to an aspect of the present invention.

In an aspect, the method will define x and y as the orthogonal spatial coordinates of the spots of a given energy in the beam's eye view (BEV) plane at the exit window of the DTC system, as shown in FIG. 25. Tissue types on the plane are defined by the functions $A_T(x,y)$ and $A_{NT}(x,y)$, which are valued at unity inside the target tissue and normal tissue, respectively, and zero otherwise. Let $D(x,y,x_s,y_s)$ be the dose distribution delivered in the BEV plane by the beam spot centered at $(x_s,y_s)$, which is assumed to be a 2-D Gaussian function for this simplified example:

$$D(x, y, x_s, y_s) = \frac{1}{2\pi\sigma_x\sigma_y}\exp\left[-\frac{1}{2}\left(\frac{(x-x_s)^2}{\sigma_x^2} + \frac{(y-y_s)^2}{\sigma_y^2}\right)\right], \quad (6)$$

where $\sigma_x$ and $\sigma_y$ define the spot width in the x and y directions, respectively.

If the positions of the x and y trimmers are $[X_1,X_2]$ and $[Y_1,Y_2]$, respectively, then $E_T$ and $E_{NT}$ are calculated on a given BEV plane as:

$$E_{T/NT}(X_1,X_2,Y_1,Y_2) = \int_{X_1}^{X_2} dx \int_{Y_1}^{Y_2} dy\ A_{T/NT}(x,y)D(x,y), \quad (7)$$

and $E_{tot}=E_T+E_{NT}$. The trimmer positions for each spot can be determined by solving the following optimization problem:

$$\underset{\{X_1,X_2,Y_1,Y_2\}}{\text{maximize}} E_T \quad (8)$$

subject to:

(a) $E_{NT} \leq \varepsilon \cdot E_{tot}$, (b) $X_1 \leq x_s \leq X_2,\ Y_1 \leq y_s \leq Y_2$ (c) $\Delta X_{min} \leq X_2 - X_1,\ \Delta Y_{min} \leq Y_2 - Y_1$, where constraint (a) ensures the spot energy deposited in normal tissue does not exceed the user-specified tolerance, constraint (b) ensures no more than half of a beam spot is occluded by any one trimmer blade, and constraint (c) ensures the aperture defined by the trimmers is not below some minimum area, $\Delta X_{min}\Delta Y_{min}$. If the target is so small that constraint (a) cannot be satisfied without violating constraint (c), then the trimmer positions are defined such that constraints (b) and (c) are satisfied.

The optimization problem defined in Equation (8) can be solved with gradient-based optimization techniques using the following derivatives:

$$\frac{\partial E_{T/NT}}{\partial X_1} = -\int_{Y_1}^{Y_2} dy A_{T/NT}(X_1, y)D(X_1, y) \quad (9)$$

$$\frac{\partial E_{T/NT}}{\partial X_2} = \int_{Y_1}^{Y_2} dy A_{T/NT}(X_2, y)D(X_2, y)$$

$$\frac{\partial E_{T/NT}}{\partial Y_1} = -\int_{X_1}^{X_2} dx A_{T/NT}(x, Y_1)D(x, Y_1)$$

$$\frac{\partial E_{T/NT}}{\partial Y_2} = \int_{X_1}^{X_2} dx A_{T/NT}(x, Y_2)D(x, Y_2).$$

Figure 26:
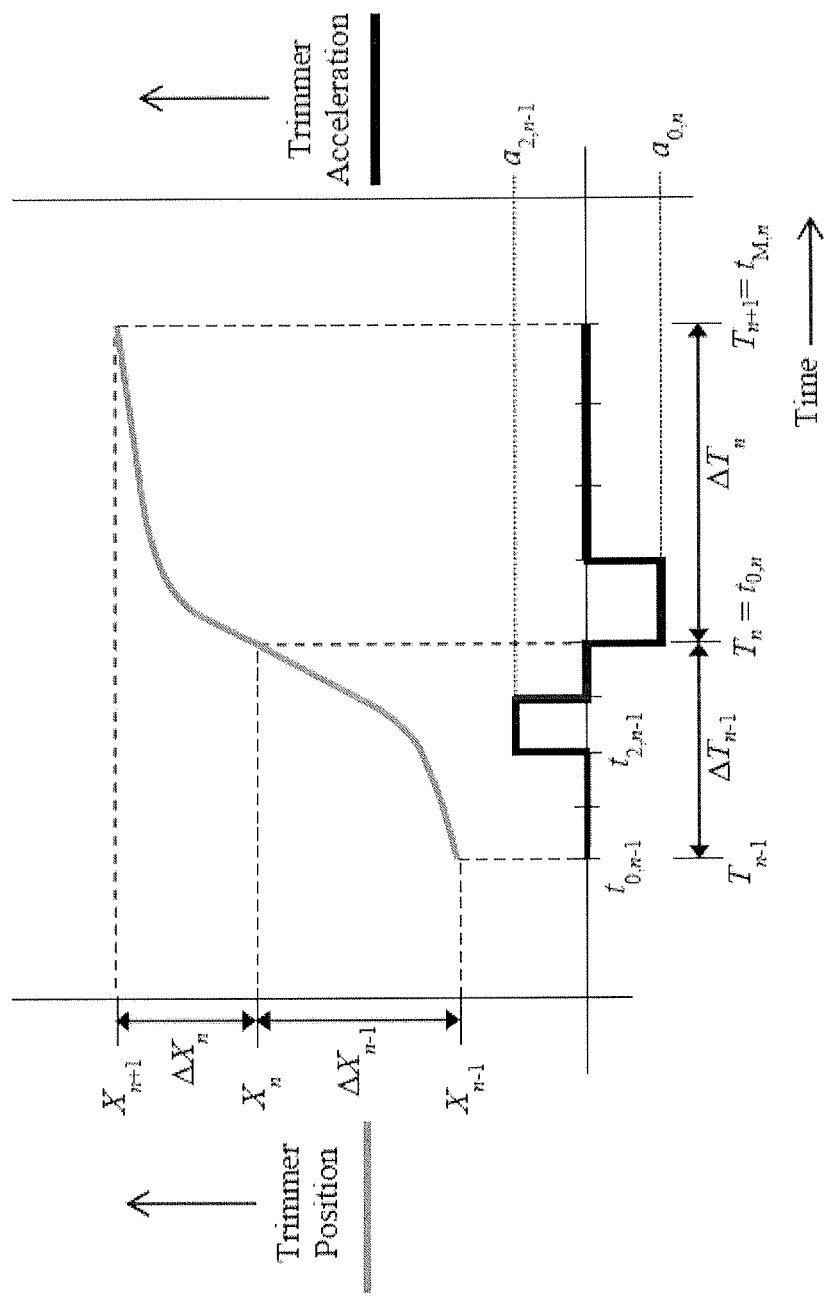
FIG. 26 is a trimmer trajectory model according to an aspect of the present invention.

The trimmer needs to be in position to intercept the beam when it arrives at its predetermined position. This is accomplished using the trajectory model described in this section. A diagram of the trimmer trajectory model is shown in FIG. 26. As shown, the trimmer trajectory model shows time, trimmer position, and acceleration, but not velocity. $X_n$ is the trimmer position at time $T_n$, where n is the trimmer travel interval index. Each travel interval is divided into M sub-intervals, and $t_{m,n}$ is the time at the beginning of sub-interval m of travel interval n. The acceleration is applied uniformly over a given sub-interval, and $a_{0,n}$ is the acceleration between times $t_{0,n}$ and $t_{1,n}$.

Suppose the positions that need be visited by a given trimmer edge are given by $X_n$, where $n \in [0, N-1]$ is the position index. Let $T_n$, $V_n$, and $A_n$ be the time, velocity, and acceleration, respectively, of the trimmer when it is at position n. Define $\Delta X_n = X_{n+1} - X_n$ and $\Delta T_n = T_{n+1} - T_n$ as the trimmer travel interval and travel time, respectively, between positions n and n+1, and define $\Delta X_{N-1} = \Delta T_{N-1} = 0$. The time, $T_n$, when the trimmer edge is at position n, and the edge position, $X_n$ can be calculated as:

$$T_n = T_0 + \sum_{n'=0}^{n-1} \Delta T_{n'}, \text{ and } X_n = X_0 + \sum_{n'=0}^{n-1} \Delta X_{n'}. \quad (10)$$

and the total trimmer travel time for all N positions is $T_{N-1}$.

Divide the travel time $\Delta T_n$ into integer M sub-intervals of equal length and define the fine-resolution time, $t_{m,n}$, as:

$$t_{m,n} = T_n + \frac{\Delta T_n}{M} m. \quad (11)$$

Wherein $n \in [0, M-1]$ and define $a_{m,n}$ as the constant trimmer acceleration between time $t_{m,n}$ and $t_{m+1,n}$. The trimmer velocity and position at time $t_{m,n}$ are thus:

$$v_{m,n} = V_n + \frac{\Delta T_n}{M} \sum_{m'=0}^{m-1} a_{m',n}, \text{ and} \quad (12)$$

$$x_{m,n} = X_n + \frac{\Delta T_n}{M} \sum_{m'=0}^{m-1} v_{m',n} + \frac{1}{2} \frac{\Delta T_n^2}{M^2} \sum_{m'=0}^{m-1} a_{m',n}.$$

respectively, therefore:

$$T_{n+1} = t_{M,n} = t_{0,n+1}, V_{n+1} = v_{M,n} = v_{0,n+1}, \text{ and } X_{n+1} = x_{M,n} = x_{0,n+1}, \quad (13)$$

The trimmer travel distance can be expressed as a function of acceleration, velocity, and travel time by substituting $v_{m,n}$ into $x_{m,n}$ in Equation (12), then setting $x_{m,n}$ to $x_{M,n} = X_{n+1}$ using Equation (13) to obtain:

$$\Delta X_n = X_{n+1} - X_n = V_n \Delta T_n - \gamma_n \Delta T_n^2. \quad (14)$$

where $$\gamma_n = \frac{1}{M^2} \sum_{m=0}^{M-2} \sum_{m'=0}^{m} a_{m',n} + \frac{1}{2} \frac{1}{M^2} \sum_{m=0}^{M-1} a_{m,n}. \quad (15)$$

For the case in which the acceleration is a constant $A_n$ during interval n, $a_{m',n} = A_n$ for $m' \in [0, M-1]$, $\gamma_n = 1/2 A_n$, and Equation (14) reduces to the familiar kinematic equation. Equation (14) can be solved for $\Delta T_n$ using the quadratic formula to obtain:

$$\Delta T_n = \frac{-V_n \pm \sqrt{V_n^2 + 4 \Delta X_n \gamma_n}}{2 \gamma_n}, \quad (16)$$

Enabling the straight forward calculation of $T_n$ with Equation (10).

The trimmer motion optimization problem is that of finding elements, $a_{m,n}$, of the acceleration matrix, a, that minimize the total trimmer travel time $T_{N-1}$. The problem can be formulated as follows:

$$\underset{a}{\text{minimize}} T_{N-1} \quad (17)$$

subject to:

(a) $V_0 = V_{N-1} = 0$ (b) $V_n = 0$ if $\text{sgn}(\Delta X_{n-1}) = -\text{sgn}(\Delta X_n)$ for $n = 1, \ldots, N-2$ (c) $0 \leq \Delta T_n$ for $n = 0, \ldots, N-1$ (d) $|a_{mn}| \leq A_{max}$ for $m = 0, \ldots, M-1$ and $n = 0, \ldots, N-1$ (e) $|v_{mn}| \leq V_{max}$ for $m = 0, \ldots, M-1$ and $n = 0, \ldots, N-1$.

(f) $V_n^2 + 4 \Delta X_n \gamma_n \geq 0$

Constraint (a) forces the velocity to be zero for the first and last trimmer positions, and constraint (b) forces the velocity to be zero at positions where the trimmer motion direction change. The sgn(x) function returns the sign of x, and is −1 if x<0, 0 if x=0, and 1 if x>0. Constraint (c) ensures all travel times are non-negative. Constraints (d) and (e) ensure the trimmer acceleration and velocity magnitudes remain below their mechanically-dictated maxima of Amax and Vmax, respectively. Constraint (f) ensures that the derivatives of $\Delta T_n$ with respect to $\gamma_n$ and $V_n$, do not diverge, and that $\Delta T_n$ is real.

An initial guess for a that satisfies all of the constraints in Equation (17) can be calculated as follows. Let M=2, $V_n=0$, and $a_{0,n} = -a_{1,n}$ for all n. Then $\gamma_n = a_{0,n} \Delta T_n/2$ and $\Delta X_n = a_0$, $n \Delta T_n^2/4 = v_{1,n} \Delta T_n/2$. If one assigns $a_{0,n} = \text{sgn}(\Delta X_n) A_{max}$, then $\Delta T_n = \sqrt{4 \Delta X_n / a_{0,n}}$, and if $V_{max} < v_{1,n}$, then one can assign $v_{1,n} = V_{max}$, calculate a new $\Delta T_n = |2 \Delta X_n / V_{max}|$ and reassign $a_{0,n} = 4 \Delta X_n / \Delta T_n^2 = V_{max}^2 / \Delta X_n$. The initial guess can be extended to the case of any M that is a multiple by resampling.

In the current section, the expression for the gradient of $T_{N-1}$ with respect to a is provided, and then each component of the expression is derived. The derivative of $T_{N-1}$ with respect to $a_{m,n}$ is calculated as follows:

$$\frac{\partial T_{N-1}}{\partial a_{m,n}} = \sum_{n'=n}^{N-1} \frac{\partial \Delta T_{n'}}{\partial a_{m,n}}, \quad (18)$$

where $$\frac{\partial \Delta T_{n'}}{\partial a_{m,n}} = \begin{cases} \dfrac{M-m-1/2}{M^2} \cdot \dfrac{\partial \Delta T_n}{\partial \gamma_n} & \text{for } n' = n \\ \dfrac{\partial \Delta T_{n'}}{\partial V_{n'}} \cdot \dfrac{\partial V_{n'}}{\partial a_{m,n}} & \text{for } n' > n \end{cases} \quad (19)$$

The components of Equation (19) are the following:

$$\frac{\partial \Delta T_n}{\partial \gamma_n} = \begin{cases} \pm \frac{\Delta X_n}{\gamma_n \sqrt{V_n^2 + 4\Delta X_n \gamma_n}} - \frac{-V_n \pm \sqrt{V_n^2 + 4\Delta X_n \gamma_n}}{2\gamma_n^2} & \text{when } \gamma_n \neq 0 \\ -\frac{\Delta X_n^2}{V_n^3} & \text{when } \gamma_n = 0 \end{cases}, \quad (20)$$

$$\frac{\partial \Delta T_{n'}}{\partial a_{m,n}} = \begin{cases} \frac{-1 \pm V_{n'}(V_{n'}^2 + 4\Delta X_{n'} \gamma_{n'})^{-\frac{1}{2}}}{2\gamma_{n'}} & \text{when } \gamma_{n'} \neq 0 \\ -\frac{\Delta X_{n'}}{V_{n'}^2} & \text{when } \gamma_{n'} = 0 \end{cases}, \quad (21)$$

and $$\frac{\partial V_{n'}}{\partial a_{m,n}} = \begin{cases} \frac{\Delta T_n}{M} + \bar{a}_n \frac{\partial \Delta T_n}{\partial a_{m,n}} & \text{for } n' = n+1 \\ \left(1 + \bar{a}_{n'-1} \frac{\partial \Delta T_{n'-1}}{\partial V_{n'-1}}\right) \frac{\partial V_{n'-1}}{\partial a_{m,n}} & \text{for } n' > n+1 \end{cases}, \quad (22)$$

where $$\bar{a}_n = \frac{1}{M} \sum_{m=0}^{M-1} a_{m,n} \quad (23)$$

is the average acceleration during interval n. The calculation of Equation (19) is a recursive process, as Equation (22) for the case of n'=n+1 depends on Equation (19) for the case of n'=n, and Equation (22) for the case of n'>n+1 depends on Equation (22) for the case of n'−1.

Constraints (a) and (b) have the following derivatives:

$$\frac{\partial \Delta V_{n'}}{\partial a_{m,n}} = \frac{\partial \Delta v_{0,n'}}{\partial a_{m,n}}, \quad (24)$$

where $$\frac{\partial \Delta v_{m',n'}}{\partial a_{m,n}} = \begin{cases} 0 & \text{for } n' < n \\ \frac{\partial \Delta T_n}{\partial a_{m,n}} \cdot \frac{1}{M} \sum_{m''=0}^{m'-1} a_{m'',n} + \frac{\Delta T_n}{M} H(m'-m) & \text{for } n' = n \\ \frac{\partial V_{n'}}{\partial a_{m,n}} + \frac{\partial \Delta T_{n'}}{\partial a_{m,n}} \cdot \frac{1}{M} \sum_{m''=0}^{m'-1} a_{m'',n} & \text{for } n' > n \end{cases} \quad (25)$$

Constraint (e) can be rewritten as:

$$|v_{m,n}| = v_{m,n} sgn(v_{m,n}) \leq V_{max}, \quad (26)$$

thus the derivative of constraint (e) with respect to $a_{m,n}$ is:

$$\frac{\partial |v_{m',n'}|}{\partial a_{m,n}} = \quad (27)$$

$$\frac{\partial \Delta v_{m',n'}}{\partial a_{m,n}} sgn(v_{m',n'}) + 2v_{m',n'} \delta(v_{m',n'}) = \frac{\partial \Delta v_{m',n'}}{\partial a_{m,n}} sgn(v_{m',n'}).$$

The derivative of constraint (f) is:

$$\frac{\partial}{\partial a_{m,n}}(V_{n'}^2 + 4\Delta X_{n'} \gamma_{n'}) = \begin{cases} 0 & \text{for } n' < n \\ 2V_{n'} \frac{\partial V_{n'}}{\partial a_{m,n}} + \begin{cases} 4\Delta X_n \frac{\partial \gamma_n}{\partial a_{m,n}} & \text{for } n' = n \\ 0 & \text{for } n' > n \end{cases} \end{cases} \quad (28)$$

The second partial derivative in Equation (29) can be calculated by rewriting $\gamma_n$ in Equation (15) to reveal where the $a_{m,n}$ is located in the summations:

$$\gamma_n = \frac{1}{M^2} \left[ \sum_{m'=0}^{m-1} \sum_{m''=0}^{m'} a_{m'',n} + \sum_{m'=m}^{M-2} \left( \sum_{m''=0}^{m-1} a_{m'',n} + a_{m,n} + \sum_{m''=m+1}^{m'} a_{m'',n} \right) + \frac{1}{2} \sum_{m'=0}^{M-1} a_{m',n} \right]. \quad (30)$$

The first term on the right hand side of Equation (30) is independent of $a_{m,n}$ and so are the first and third terms (summations) inside the parentheses, thus then derivatives with respect to $a_{m,n}$ vanish and one obtains:

$$\frac{\partial \gamma_n}{\partial a_{m,n}} = \frac{1}{M^2} \left[ \sum_{m'=m}^{M-2} 1 + \frac{1}{2} \right] = \frac{M - m - 1/2}{M^2}. \quad (31)$$

Equation (19) is obtained by applying the chain rule as follows:

$$\frac{\partial \Delta T_n}{\partial a_{m,n}} = \frac{\partial \Delta T_n}{\partial \gamma_n} \frac{\partial \gamma_n}{\partial a_{m,n}}. \quad (29)$$

The second partial derivative in Equation (29) can be calculated by rewriting $\gamma_n$ in Equation (15) to reveal where $a_{m,n}$ is located in the summations:

$$\gamma_n = \frac{1}{M^2} \left[ \sum_{m'=0}^{m-1} \sum_{m''=0}^{m'} a_{m'',n} + \sum_{m'=m}^{M-2} \left( \sum_{m''=0}^{m-1} a_{m'',n} + a_{m,n} + \sum_{m''=m+1}^{m'} a_{m'',n} \right) + \frac{1}{2} \sum_{m'=0}^{M-1} a_{m',n} \right]. \quad (30)$$

The first term on the right hand side of Equation (30) is independent of $a_{m,n}$, and so are the first and third terms (summations) inside the parentheses, thus the derivatives with respect to $a_{m,n}$ vanish and one obtains:

$$\frac{\partial \gamma_n}{\partial a_{m,n}} = \frac{1}{M^2} \left[ \sum_{m'=m}^{M-2} 1 + \frac{1}{2} \right] = \frac{M - m - 1/2}{M^2}. \quad (31)$$

Differentiating Equation (16) with respect to $\gamma_n$ and $V_n$ produces Equation (20) and Equation (21), respectively, for the case of a non-zero $\gamma_n$. Applying L'Hôpital's rule to those results, when the "±" is negative, yields Equation (20) and Equation (21) for the case when $\gamma_n$ is zero. Equation (22) for the case of n'=n+1 is obtained by setting m=M in Equation (12), thus $v_{m,n}=v_{M,n}=V_{n+1}=V_{n'}$, and differentiating the result with respect to $a_{m,n}$ under the recognition that $\Delta T_n$ is dependent on $a_{m,n}$. Equation (22) for the case of n'>n+1 is obtained using the chain rule:

$$\frac{\partial V_{n'}}{\partial a_{m,n}} = \frac{\partial V_{n'}}{\partial V_{n'-1}} \frac{\partial V_{n'-1}}{\partial a_{m,n}}. \quad (32)$$

The first partial derivative on the right hand side of Equation is obtained by setting $v_{m,n}=v_{M,n'-1}=V_{n'}$ in Equation (12) and then differentiating the result with respect to $V_{n'-1}$. The second partial derivative in Equation (32) (as in Equation (22)) is obtained recursively from the evaluation of Equation (22) from the previous n' value.

Figure 27:
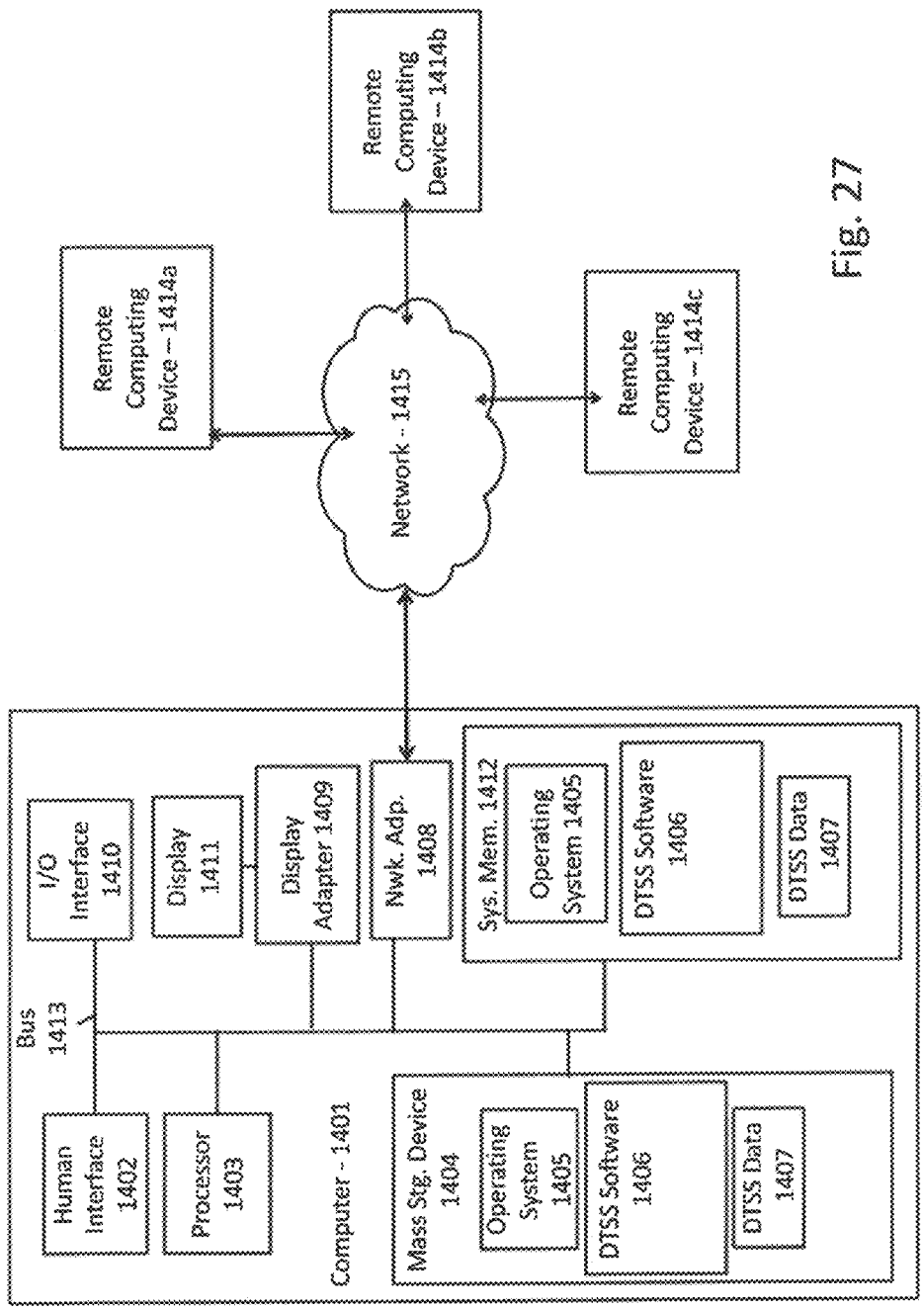
FIG. 27 is a block diagram of a computer according to an aspect of the present invention.

FIG. 27 is a block diagram illustrating an exemplary operating environment for performing a portion of disclosed methods according to an embodiment of the present invention. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

Further, one skilled in the art will appreciate that the systems and methods disclosed herein can utilize a general-purpose computing device in the form of a computer 1401. The methods discussed above can be performed by the computer 1401. For example, the computer 1401 can perform the duties and responsibilities of the controller 60 discussed above in FIGS. 1-2. Further, the computer 1401 can perform and control the responsibilities of the irradiation controller 62, the SS system controller 64, and the position planning controller 66 discussed above.

The components of the computer 1401 can comprise, but are not limited to, one or more processors or processing units 1403, a system memory 1412, and a system bus 1413 that couples various system components including the processor 1403 to the system memory 1412. In the case of multiple processing units 1403, the system can utilize parallel computing.

The system bus 1413 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 1413, and all buses specified in this description can also be implemented over a wired or wireless network connection and each of the subsystems, including the processor 1403, a mass storage device 1404, an operating system 1405, DTSS software 1406, DTSS data 1407, a network adapter 1408, system memory 1412, an Input/Output Interface 1410, a display adapter 1409, a display device 1411, and a human machine interface 1402, can be contained within one or more remote computing devices 1414a,b,c at physically separate locations, connected through buses of this form, in effect implementing a fully distributed system.

The computer 1401 typically comprises a variety of computer readable media. Exemplary readable media can be any available media that is accessible by the computer 1401 and comprises, for example and not meant to be limiting, both volatile and non-volatile media, removable and non-removable media. The system memory 1412 comprises computer readable media in the form of volatile memory, such as random access memory (RAM), and/or non-volatile memory, such as read only memory (ROM). The system memory 1412 typically contains data such as DTSS data 1407 and/or program modules such as operating system 1405 and DTSS software 1406 (i.e., controlling the various controllers 60 and modules 62, 64, 66 discussed above) that are immediately accessible to and/or are presently operated on by the processing unit 1403.

In another aspect, the computer 1401 can also comprise other removable/non-removable, volatile/non-volatile computer storage media. By way of example, FIG. 27 illustrates a mass storage device 1404, which can provide non-volatile storage of computer code, computer readable instructions, data structures, program modules, and other data for the computer 1401. For example and not meant to be limiting, a mass storage device 1404 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 1404, including by way of example, an operating system 1405 and DTSS software 1406. Each of the operating system 1405 and DTSS software 1406 (or some combination thereof) can comprise elements of the programming and the DTSS software 1406. DTSS data 1407 can also be stored on the mass storage device 1404. DTSS data 1407 can be stored in any of one or more databases known in the art. Examples of such databases include DB2®, Microsoft® Access, Microsoft® SQL Server, Oracle®, mySQL, PostgreSQL, and the like. The databases can be centralized or distributed across multiple systems.

In another aspect, the user can enter commands and information into the computer 1401 via an input device (not shown). Examples of such input devices comprise, but are not limited to, a keyboard, pointing device (e.g., a "mouse"), a microphone, a joystick, a scanner, tactile input devices such as gloves, and other body coverings, and the like. These and other input devices can be connected to the processing unit 1403 via a human machine interface 1402 that is coupled to the system bus 1413, but can be connected by other interface and bus structures, such as a parallel port, game port, an IEEE 1394 Port (also known as a Firewire port), a serial port, or a universal serial bus (USB).

In yet another aspect, a display device 1411 can also be connected to the system bus 1413 via an interface, such as a display adapter 1409. It is contemplated that the computer 1401 can have more than one display adapter 1409 and the computer 1401 can have more than one display device 1411. For example, a display device can be a monitor, an LCD (Liquid Crystal Display), or a projector. In addition to the display device 1411, other output peripheral devices can comprise components such as speakers (not shown) and a printer (not shown) which can be connected to the computer 1401 via Input/Output Interface 1410. Any step and/or result of the methods can be output in any form to an output device. Such output can be any form of visual representation, including, but not limited to, textual, graphical, animation, audio, tactile, and the like.

The computer 1401 can operate in a networked environment using logical connections to one or more remote computing devices 1414a,b,c. By way of example, a remote computing device can be a personal computer, a laptop computer, portable computer, a server, a router, a network computer, a peer device or other common network node, and so on. Logical connections between the computer 1401 and a remote computing device 1414a,b,c can be made via a local area network (LAN) and a general wide area network (WAN). Such network connections can be through a network adapter 1408. A network adapter 1408 can be implemented in both wired and wireless environments. Such networking environments are conventional and commonplace in offices, enterprise-wide computer networks, intranets, and the Internet 1415.

According to an aspect, the computer 1401, via the DTSS software 1406 and DTSS data 1407, can control the operation of the SS ion therapy system 10 according to an aspect. In another aspect, the computer 1401 can comprise the controller 60 of the present invention, as well as the various controllers (irradiation controller 62, SS system controller 64, and position planning controller 66 as discussed in reference to FIG. 2).

For purposes of illustration, application programs and other executable program components such as the operating system 1405 are illustrated herein as discrete blocks, although it is recognized that such programs and components reside at various times in different storage components of the computing device 1401, and are executed by the data processor(s) of the computer. An implementation of DTSS software 1406 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention. To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, those skilled in the art will appreciate that the within disclosures are exemplary only and that various other alternatives, adaptations, and modifications may be made within the scope of the present invention. Accordingly, the present invention is not limited to the specific embodiments as illustrated herein, but is only limited by the following claims.

REFERENCES

M. Bues, W. D. Newhauser, U. Titt and A. R. Smith, "Therapeutic step and shoot proton beam spotscanning with a multi-leaf collimator: a Monte Carlo study," Radiation protection dosimetry 115, 164-169 (2005).

A. J. Lomax, T. Bortfeld, G. Goitein, J. Debus, C. Dykstra, P. A. Tercier, P. A. Coucke and R. O. Mirimanoff, "A treatment planning inter-comparison of proton and intensity modulated photon radiotherapy," Radiother Oncol 51, 257-271 (1999).

J. D. Fontenot, A. K. Lee and W. D. Newhauser, "Risk of secondary malignant neoplasms from proton therapy and intensity-modulated x-ray therapy for early-stage prostate cancer," International journal of radiation oncology, biology, physics 74, 616-622 (2009).

ICRP, "Recommendations of the International Commission on Radiological Protection: Publication 60," N0, (1991).

E. J. Hall, Radiobiology for the Radiologist, 5 ed. (Lippincott Williams & Wilkins, Philadelphia, Pa., 2000).

R. Miralbell, L. Cella, D. Weber and A. Lomax, "Optimizing radiotherapy of orbital and paraorbital tumors: intensity-modulated X-ray beams vs. intensity-modulated proton beams," International journal of radiation oncology, biology, physics 47, 1111-1119 (2000).

R. Miralbell, A. Lomax and M. Russo, "Potential role of proton therapy in the treatment of pediatric medulloblastoma/primitive neuro-ectodermal tumors: spinal theca irradiation," International journal of radiation oncology, biology, physics 38, 805-811 (1997).

R. Miralbell, A. Lomax, L. Cella and U. Schneider, "Potential reduction of the incidence of radiation induced second cancers by using proton beams in the treatment of pediatric tumors," Int J Radiat Oncol Biol Phys 54, 824-829 (2002).

D. C. Weber, A. V. Trofimov, T. F. Delaney and T. Bortfeld, "A treatment planning comparison of intensity modulated photon and proton therapy for paraspinal sarcomas," International journal of radiation oncology, biology, physics 58, 1596-1606 (2004).

R. T. Flynn, S. R. Bowen, S. M. Bentzen, T. Rockwell Mackie and R. Jeraj, "Intensity-modulated x-ray (IMXT) versus proton (IMPT) therapy for theragnostic hypoxia-based dose painting," Phys Med Biol 53, 4153-4167 (2008).

L. Widesott, A. Pierelli, C. Fiorino, I. Dell'oca, S. Broggi, G. M. Cattaneo, N. Di Muzio, F. Fazio, R. Calandrino and M. Schwarz, "Intensity-modulated proton therapy versus helical tomotherapy in nasopharynx cancer: planning comparison and NTCP evaluation," International journal of radiation oncology, biology, physics 72, 589-596 (2008).

D. Thorwarth, M. Soukup and M. Alber, "Dose painting with IMPT, helical tomotherapy and IMXT: A dosimetric comparison," Radiother Oncol 86, 30-34 (2008).

A. J. Lomax, M. Goitein and J. Adams, "Intensity modulation in radiotherapy: photons versus protons in the paranasal sinus," Radiother Oncol 66, 11-18 (2003).

A. Trofimov, P. L. Nguyen, J. J. Coen, K. P. Doppke, R. J. Schneider, J. A. Adams, T. R. Bortfeld, A. L. Zietman, T. F. Delaney and W. U. Shipley, "Radiotherapy treatment of early-stage prostate cancer with IMRT and protons: A treatment planning comparison," Int J Radiat Oncol Biol Phys (2007).

ICRU, "Prescribing, Recording, and Reporting Proton-Beam Therapy, ICRU Report 78," in J. ICRU, Vol. 7, (Oxford University Press, UK, 2007).

A. R. Smith, "Proton therapy," Phys Med Biol 51, R491-504 (2006).

A. J. Lomax, T. Bohringer, A. Bolsi, D. Coray, F. Emert, G. Goitein, M. Jermann, S. Lin, E. Pedroni, H. Rutz, O. Stadelmann, B. Timmermann, J. Verwey and D. C. Weber, "Treatment planning and verification of proton therapy using spot scanning: initial experiences," Med Phys 31, 3150-3157 (2004).

E. Pedroni, R. Bacher, H. Blattmann, T. Bohringer, A. Coray, A. Lomax, S. Lin, G. Munkel, S. Scheib, U. Schneider and A. Tuorovsky, "The 200-MeV proton therapy project at the Paul Scherrer Institute: conceptual design and practical realization," Med Phys 22, 37-53 (1995).

E. Pedroni and H. Enge, "Beam optics design of compact gantry for proton therapy," Med Biol Eng Comput 33, 271-277 (1995).

A. Lomax, "Intensity modulation methods for proton radiotherapy," Phys Med Biol 44, 185-205 (1999).

M. T. Gillin, N. Sahoo, M. Bues, G. Ciangaru, G. Sawakuchi, F. Poenisch, B. Arjomandy, C. Martin, U. Titt, K. Suzuki, A. R. Smith and X. R. Zhu, "Commissioning of the discrete spot scanning proton beam delivery system at the University of Texas M.D. Anderson Cancer Center Proton Therapy Center, Houston," Med Phys 37, 154-163 (2010).

J. Daartz, M. Bangert, M. R. Bussiere, M. Engelsman and H. M. Kooy, "Characterization of a minimultileaf collimator in a proton beamline," Med Phys 36, 1886-1894 (2009).

S. Safai, T. Bortfeld and M. Engelsman, "Comparison between the lateral penumbra of a collimated double-scattered beam and uncollimated scanning beam in proton radiotherapy," Phys Med Biol 53, 1729-1750 (2008).

E. Shaw, C. Scott, L. Souhami, R. Dinapoli, R. Kline, J. Loeffler and N. Farnan, "Single dose radiosurgical treatment of recurrent previously irradiated primary brain tumors and brain metastases: final report of RTOG protocol 90-05," Int J Radiat Oncol Biol Phys 47, 291-298 (2000).

R. A. Siochi, "Leakage reduction for the Siemens Moduleaf," J Appl Clin Med Phys 10, 2894 (2009).

What is claimed is:

1. A spot scanning (SS) ion therapy system, comprising:
   a. an ion therapy source comprising at least one scanning magnet, the ion therapy source configured to sequentially direct a particle pencil beam to a number of spot positions in a target;
   b. a dynamic trimming collimator configured to be mounted downstream of the at least one scanning magnet of the ion therapy source, the dynamic trimming collimator comprising:
      i. at least one trimmer located downstream of the at least one scanning magnet and configured to intercept a portion of said pencil beam; and
      ii. at least one driving mechanism configured for moving said at least one trimmer; and
   c. a controller configured to control the ion therapy source to execute the sequence of spot irradiations by sequentially directing and delivering the particle pencil beam to the number of spot positions in the target and control the position of said at least one trimmer as a function of each of said number of spot positions.

2. The spot scanning ion therapy system according to claim 1, wherein said at least one driving mechanism is configured for moving said at least one trimmer along a first axis of motion.

3. The spot scanning ion therapy system according to claim 2, wherein said first axis is substantially perpendicular to said pencil beam.

4. The spot scanning ion therapy system of claim 3, wherein the at least one trimmer is further configured to move in a second axis of motion, wherein the second axis of motion is substantially parallel to said pencil beam.

5. The spot scanning ion therapy system according to claim 1 wherein said at least one driving mechanism comprises a first axis of motion and a second axis of motion for moving said at least one trimmer.

6. The spot scanning ion therapy system according to claim 5, wherein said first axis and said second axis are substantially perpendicular to said pencil beam.

7. The spot scanning ion therapy system according to claim 5 wherein said first and second axes of motion are translation axes for translating said at least one trimmer, said translation axis are non-parallel axes.

8. The spot scanning ion therapy system according to claim 5 wherein first axis of motion is a translation axis and second axis of motion is a rotation axis.

9. The spot scanning ion therapy system according to claim 5, wherein the said at least one trimmer is further configured to move in a third axis of motion, wherein the third axis of motion is substantially parallel to said pencil beam.

10. The spot scanning ion therapy system of claim 1, wherein said at least one trimmer has a thickness and shape adapted to modify the phase space of said pencil beam.

11. The spot scanning ion therapy system of claim 1, wherein said controller is further configured for receiving a signal indicating a beam on/off status information to allow motion of said at least one trimmer only when the beam is in an off status.

12. The spot scanning ion therapy system of claim 1, wherein said controller is configured for dynamically moving said at least one trimmer in synchrony with the execution of said sequence of spot irradiations.

13. The spot scanning ion therapy system of claim 1, further comprising a position planning controller configured for defining one or more of said spot irradiations, corresponding to pre-defined positions for positioning said at least one trimmer.

14. The spot scanning ion therapy system of claim 1, wherein said at least one trimmer further comprises a plurality of trimmers and wherein said at least one driving mechanism comprises a plurality of driving mechanisms that correspond to the plurality of trimmers, wherein said controller is configured for independently controlling the position of each of said plurality of trimmers as a function of said spot position.

15. The spot scanning ion therapy system of claim 1, further configured for two-dimensional delivery.

16. The spot scanning ion therapy system according to claim 1, wherein the controller is configured to receive data defining the trimmer position for each of the number of spot positions.

17. A dynamic trimming collimator comprising:
a. at least one trimmer configured to limit spillage of radiation from a two-dimensional scanning ion beam; and
b. at least one driving mechanism configured for moving the at least one trimmer;
wherein the dynamic trimming collimator is capable of being mounted downstream an ion therapy source configured to produce the two-dimensional scanning ion beam in a sequence to a number of spot positions in a target, and wherein the dynamic trimming collimator is capable of controlling the position of said at least one trimmer to limit spillage of radiation of the two-dimensional scanning ion beam at said target as a function for each of the number of spot positions.

18. The dynamic trimming collimator of claim 17, wherein the at least one trimmer is configured to limit spillage of radiation by partially blocking the two dimensional scanning ion beam.

19. The dynamic trimming collimator of claim 17, wherein the at least one trimmer is configured to move along a first path substantially perpendicular to an axis of the two dimensional scanning ion beam.

20. The dynamic trimming collimator of claim 19, wherein the at least one trimmer is further configured to move along a second path substantially parallel to the axis of the two dimensional scanning ion beam.

21. The dynamic trimming collimator of claim 20, wherein the first axis and the second axis are non-parallel to each other.

22. The dynamic trimming collimator of claim 17, wherein the at least one trimmer is further configured to move along a third path substantially parallel to the axis of the two dimensional scanning ion beam.

23. The dynamic trimming collimator of claim 19, wherein the at least one driving mechanism comprises a linear motor.

24. The dynamic trimming collimator of claim 19, wherein the at least one trimmer is configured to move in a substantially pendulous arc.

25. The dynamic trimming collimator of claim 19, wherein the at least one trimmer comprises a rectangular shape.

26. The dynamic trimming collimator of claim 19, wherein the at least one trimmer is configured to have a radiological thickness that is greater than the range of the two dimensional scanning ion beam.

27. The dynamic trimming collimator of claim 19, wherein the apparatus is configured to position the at least one trimmer approximate the skin of a patient.

28. The dynamic trimming collimator of claim 19, wherein the at least one trimmer is configured to move in synchrony with the two dimensional scanning ion beam.

29. The dynamic trimming collimator of claim 19, wherein the at least one trimmer comprises a plurality of trimmers and the at least one driving mechanism comprises a plurality of driving mechanisms, wherein at least each of the plurality of trimmers is associated with at least one of the plurality of driving mechanisms.

30. The dynamic trimming collimator of claim 29, wherein at least one of the plurality of trimmers is associated with at least two driving mechanisms.

31. The dynamic trimming collimator of claim 17, further comprising a range shifter.

32. The dynamic trimming collimator of claim 17, further comprising a ridge filter.

33. The dynamic trimming collimator of claim 17, wherein the dynamic trimming collimator is further configured to attach to a nozzle of the ion therapy source.

* * * * *